(12) United States Patent
Sowden

(10) Patent No.: US 7,217,381 B2
(45) Date of Patent: May 15, 2007

(54) SYSTEMS, METHODS AND APPARATUSES FOR MANUFACTURING DOSAGE FORMS

(75) Inventor: Harry S. Sowden, Glenside, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 345 days.

(21) Appl. No.: 10/745,084

(22) Filed: Dec. 23, 2003

(65) Prior Publication Data

US 2004/0175425 A1 Sep. 9, 2004

Related U.S. Application Data

(63) Continuation-in-part of application No. 09/966,939, filed on Sep. 28, 2001, now Pat. No. 6,837,696, and a continuation-in-part of application No. 10/432,812, filed on Dec. 4, 2003.

(51) Int. Cl.
*B29C 45/14* (2006.01)
*B29C 70/68* (2006.01)

(52) U.S. Cl. .................. 264/250; 264/275; 264/279.1; 425/112; 425/116; 425/125; 425/129.1

(58) Field of Classification Search ............... 425/112, 425/116, 125, 129.1; 264/250, 275, 279.1
See application file for complete search history.

(56) References Cited

U.S. PATENT DOCUMENTS

| | | |
|---|---|---|
| 599,865 A | 1/1898 | Richards |
| 2,307,371 A | 1/1943 | Hileman |
| 2,849,985 A | 9/1958 | Stott |
| 2,946,298 A | 7/1960 | Doepel et al. |
| 3,096,248 A | 7/1963 | Rudzki |
| 3,146,169 A | 8/1964 | Stephenson et al. |
| 3,177,280 A * | 4/1965 | Ford et al. ................ 264/275 |
| 3,432,592 A | 3/1969 | Speiser |
| 3,726,622 A | 4/1973 | DeTroyer et al. |
| 3,804,570 A | 4/1974 | Hoschele et al. |
| 3,832,252 A | 8/1974 | Higuchi et al. |

(Continued)

FOREIGN PATENT DOCUMENTS

DE 27 10 307 A1 9/1997

(Continued)

OTHER PUBLICATIONS

Catellani et al., Int. J. Pharmaceutics, 88 (1992) 285-291, "Centrifugal die filling system in a new rotary tablet machine."

(Continued)

*Primary Examiner*—Robert B. Davis
(74) *Attorney, Agent, or Firm*—David R. Crichton

(57) ABSTRACT

Systems, methods and apparatuses for manufacturing dosage forms, and to dosage forms made using such systems, methods and apparatuses are provided. Novel compression, injection molding, and thermal setting molding modules are disclosed. One or more of such modules may be linked, preferably via a transfer device, into an overall system for making dosage forms. The injection molding module having at least one mold shell with an interior surface capable of producing non-uniform coatings over compressed cores or molded inserts contained therein.

19 Claims, 20 Drawing Sheets

U.S. PATENT DOCUMENTS

| | | |
|---|---|---|
| 4,139,589 A | 2/1979 | Beringer et al. |
| 4,230,693 A | 10/1980 | Izzo et al. |
| 4,271,206 A | 6/1981 | Fariel et al. |
| 4,273,793 A | 6/1981 | Fariel et al. |
| 4,292,017 A | 9/1981 | Doepel |
| 4,371,516 A | 2/1983 | Gregory et al. |
| 4,372,942 A | 2/1983 | Cimiluca |
| 4,392,493 A | 7/1983 | Niemeijer |
| 4,473,526 A | 9/1984 | Buhler et al. |
| 4,518,335 A | 5/1985 | Pujari |
| 4,544,345 A | 10/1985 | Buhler et al. |
| 4,569,650 A | 2/1986 | Kramer |
| 4,686,212 A | 8/1987 | Ducatman et al. |
| 4,744,741 A | 5/1988 | Glover et al. |
| 4,749,575 A | 6/1988 | Rotman |
| 4,757,090 A | 7/1988 | Salpekar et al. |
| 4,762,719 A | 8/1988 | Forester |
| 4,781,714 A | 11/1988 | Eckenhoff et al. |
| 4,813,818 A | 3/1989 | Sanzone |
| 4,820,524 A | 4/1989 | Berta |
| 4,851,226 A | 7/1989 | Julian et al. |
| 4,882,167 A | 11/1989 | Jang |
| 4,898,733 A | 2/1990 | DePrince et al. |
| 4,929,446 A | 5/1990 | Bartolucci |
| 4,965,027 A | 10/1990 | Takahashi |
| 4,980,169 A | 12/1990 | Oppenheimer et al. |
| 5,006,297 A * | 4/1991 | Brown et al. ............... 264/234 |
| 5,059,112 A | 10/1991 | Wieser |
| 5,073,379 A | 12/1991 | Klimesch et al. |
| 5,075,114 A | 12/1991 | Roche |
| 5,089,270 A | 2/1992 | Hampton et al. |
| 5,146,730 A | 9/1992 | Sadek et al. |
| 5,200,191 A | 4/1993 | Steele et al. |
| 5,213,738 A | 5/1993 | Hampton et al. |
| 5,213,808 A | 5/1993 | Bar-Shalom et al. |
| 5,228,916 A | 7/1993 | Berta |
| 5,229,164 A | 7/1993 | Pins et al. |
| 5,368,863 A | 11/1994 | Eckenhoff et al. |
| 5,391,378 A | 2/1995 | Sanderson |
| 5,415,868 A | 5/1995 | Smith et al. |
| 5,436,026 A | 7/1995 | Berta |
| 5,459,983 A | 10/1995 | Sadek et al. |
| 5,464,631 A | 11/1995 | Hoover et al. |
| 5,489,436 A | 2/1996 | Hoy et al. |
| 5,511,361 A | 4/1996 | Sauter |
| 5,538,125 A | 7/1996 | Berta |
| 5,578,336 A | 11/1996 | Monte |
| 5,609,010 A | 3/1997 | Sauter |
| 5,614,207 A | 3/1997 | Shah et al. |
| 5,679,406 A | 10/1997 | Berta |
| 5,681,584 A | 10/1997 | Savastano et al. |
| 5,795,588 A | 8/1998 | Sauter |
| 5,824,338 A | 10/1998 | Jacobs et al. |
| 5,827,548 A * | 10/1998 | Lavallee et al. ............ 425/116 |
| 5,830,501 A | 11/1998 | Dong et al. |
| 5,830,502 A | 11/1998 | Dong et al. |
| 5,834,035 A | 11/1998 | Osada et al. |
| 5,837,301 A | 11/1998 | Arnott et al. |
| 5,853,760 A | 12/1998 | Cremer |
| 5,871,781 A | 2/1999 | Myers et al. |
| 5,897,910 A | 4/1999 | Rosenberg et al. |
| 5,942,034 A | 8/1999 | Brehant et al. |
| 5,997,905 A | 12/1999 | McTeigue et al. |
| 6,001,391 A | 12/1999 | Zeidler et al. |
| 6,103,257 A | 8/2000 | Nisonoff |
| 6,117,479 A | 9/2000 | Hogan et al. |
| 6,149,939 A | 11/2000 | Strumor et al. |
| 6,149,943 A | 11/2000 | McTeigue et al. |
| 6,200,590 B1 | 3/2001 | Eley |
| 6,248,760 B1 | 6/2001 | Wilhelmsen |
| 6,350,398 B1 | 2/2002 | Breitenbach et al. |
| 6,365,185 B1 | 4/2002 | Ritschel et al. |
| 6,394,094 B1 | 5/2002 | McKenna et al. |
| 6,837,696 B2 * | 1/2005 | Sowden et al. ............. 425/112 |
| 2001/0001280 A1 | 5/2001 | Dong et al. |
| 2002/0028240 A1 | 3/2002 | Sawada et al. |

FOREIGN PATENT DOCUMENTS

| | | |
|---|---|---|
| EP | 0 088 556 B1 | 9/1983 |
| EP | 0 239 983 B1 | 10/1987 |
| EP | 0 294 993 B1 | 12/1988 |
| EP | 0 481 547 A1 | 4/1992 |
| EP | 0611032 A1 | 9/1994 |
| EP | 0 788 790 A2 | 8/1997 |
| EP | 0 861 659 A1 | 9/1998 |
| EP | 0 950 402 B1 | 10/1999 |
| EP | 1 077 065 A1 | 2/2001 |
| FR | 2 604 904 A1 | 4/1988 |
| GB | 759 081 A | 10/1956 |
| GB | 888 038 | 1/1962 |
| GB | 936 386 | 9/1963 |
| GB | 994 742 | 6/1965 |
| GB | 1 144 915 | 3/1969 |
| GB | 1 372 040 | 10/1974 |
| GB | 1 510 772 | 5/1978 |
| GB | 2 197 778 A | 6/1988 |
| JP | 03261719 A | 11/1991 |
| NL | 8602556 | 5/1988 |
| WO | WO 9406416 A1 | 3/1994 |
| WO | WO 9407470 A1 | 4/1994 |
| WO | WO 95/02396 | 1/1995 |
| WO | WO 9502396 A1 | 1/1995 |
| WO | WO 9706695 A1 | 2/1997 |
| WO | WO 9715293 A2 | 5/1997 |
| WO | WO 9902136 A1 | 1/1999 |
| WO | WO 9951209 A1 | 10/1999 |
| WO | WO 9956730 A1 | 11/1999 |
| WO | WO 0018447 A2 | 4/2000 |
| WO | WO 0115889 A1 | 3/2001 |
| WO | WO 03020246 A1 | 3/2003 |

OTHER PUBLICATIONS

Cuff & Rauf, Pharm Tech, Jun. 1998, 96-106, "A Preliminary Evaluation of Injection Molding as a Technology to Produce Tablets."

Eith, L., et al., "Injection-Moulded Drug-Delivery Systems", Manufacturing Chemist (Jan. 1987), pp. 21-25.

Lachman, Leon, et al., "Chapter II—Tablets", The Theory and Practice of Industrial Pharmacy (1986), pp. 293-345.

Rosato, Dominick & Donald, "Injection Molding Handbook", The Complete Molding Operation Technology, Performance, Economics (1986), pp. 189-191 & 794-795.

PCT Search Report for PCT/US 02/30614 dated Feb. 26, 2003.

* cited by examiner

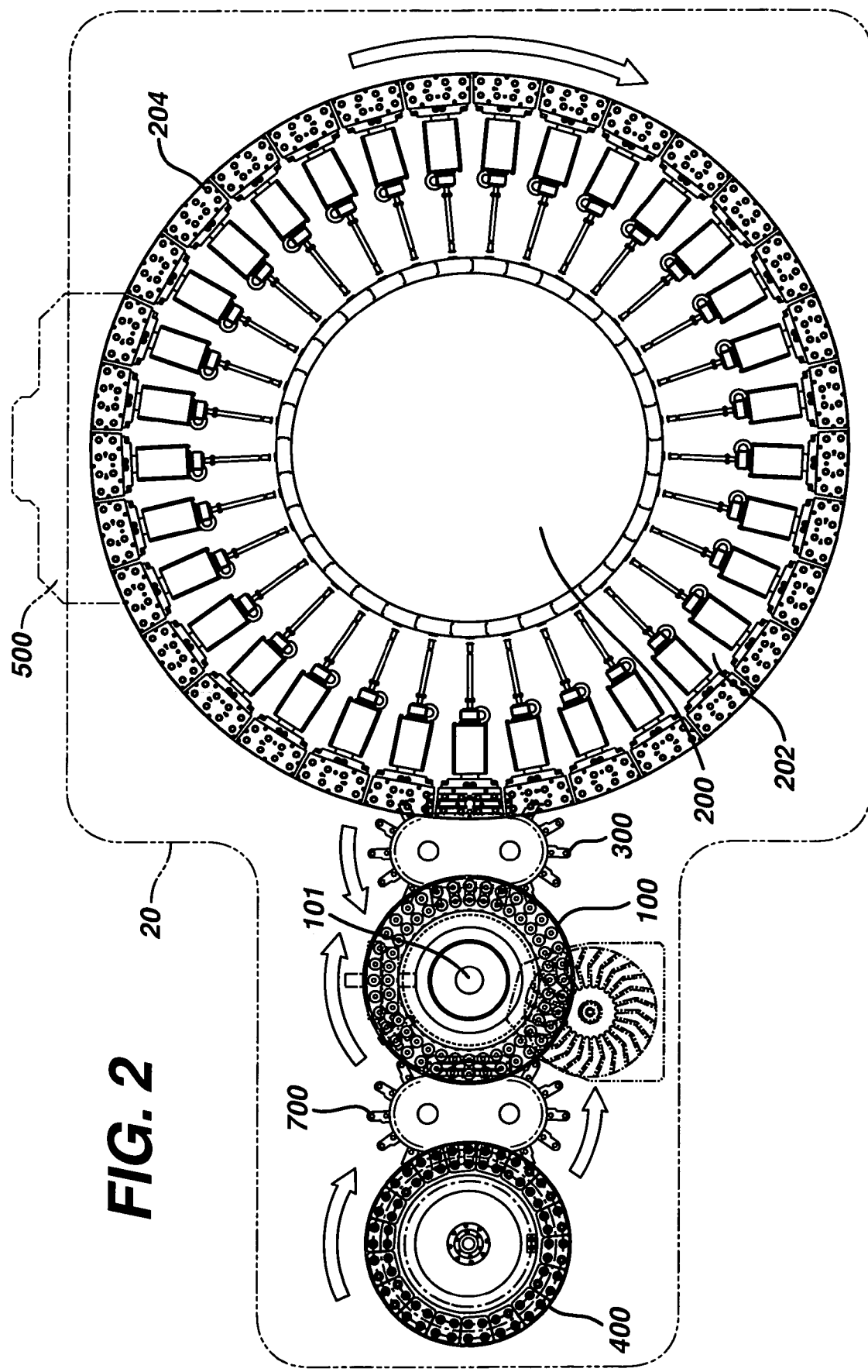

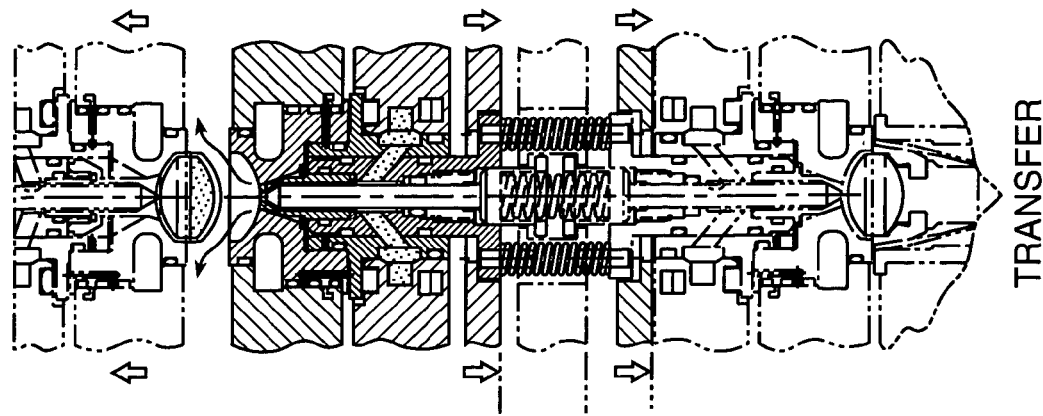
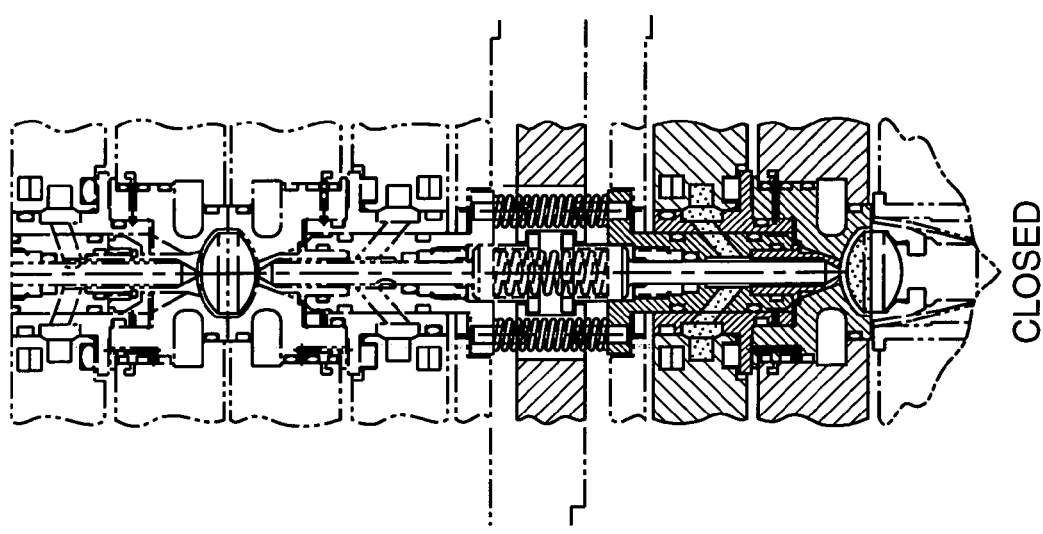
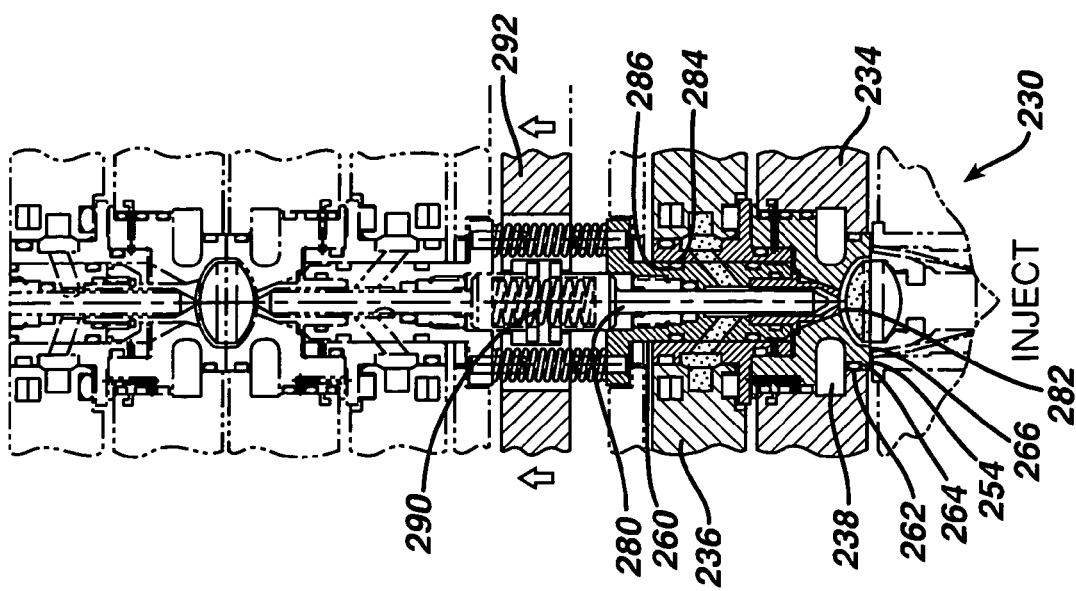

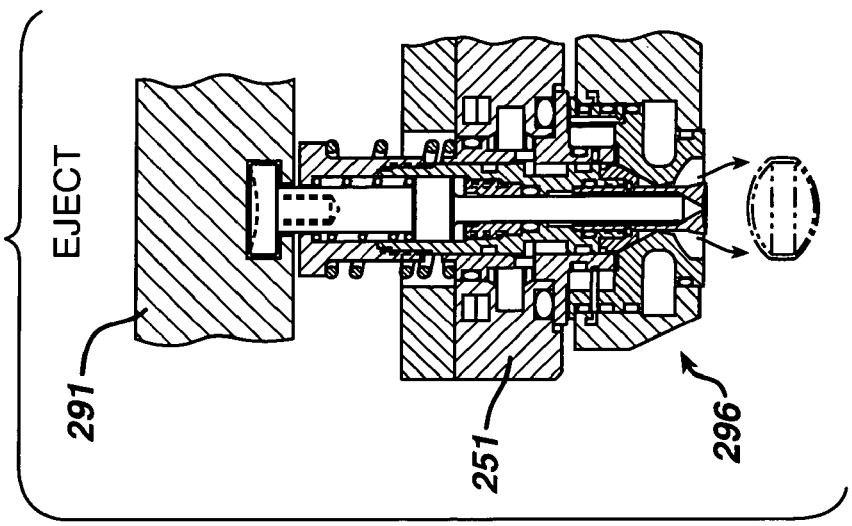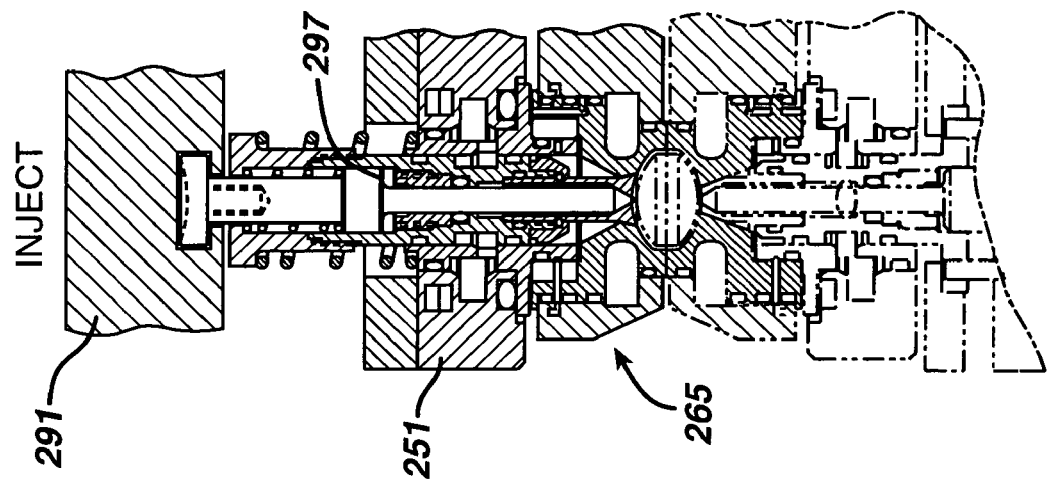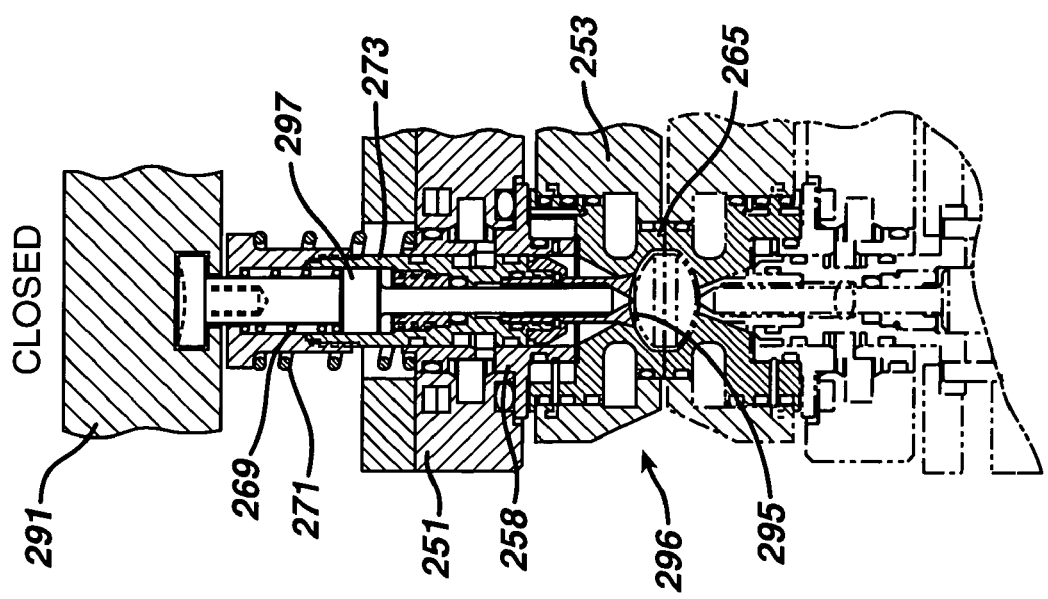

SYSTEMS, METHODS AND APPARATUSES FOR MANUFACTURING DOSAGE FORMS

This application is a continuation-in-part of U.S. Ser. No. 09/966,939, filed on Sep. 28, 2001 and now U.S. Pat. No. 6,837,696, and U.S. Ser. No. 10/432,812, filed on Dec. 4 2003.

FIELD OF THE INVENTION

This invention relates generally to systems, methods and apparatuses for manufacturing dosage forms, and to dosage forms made using such systems, methods and apparatuses.

BACKGROUND OF THE INVENTION

A variety of dosage forms, such as tablets, capsules and gelcaps are known in the pharmaceutical arts. Tablets generally refer to relatively compressed powders in various shapes. One type of elongated, capsule-shaped film coated tablet is commonly referred to as a "caplet." Capsules are typically manufactured using a two-piece gelatin shell formed by dipping a steel rod into gelatin so that the gelatin coats the end of the rod. The gelatin is hardened into two half-shells and the rod extracted. The hardened half-shells are then filled with a powder and the two halves joined together to form the capsule. (See Generally, Howard C. Ansel et al., Pharmaceutical Dosage Forms And Drug Delivery Systems (7th Ed. 1999).)

Gelatin-coated tablets, commonly known as geltabs and gelcaps, are an improvement on gelatin capsules and typically comprise a tablet coated with a gelatin shell. Several well known examples of gelcaps are McNeil Consumer Healthcare's acetaminophen based products sold under the trade name Tylenol®. U.S. Pat. Nos. 4,820,524; 5,538,125; 5,228,916; 5,436,026; 5,679,406; 5,415,868; 5,824,338; 5,089,270; 5,213,738; 5,464,631; 5,795,588; 5,511,361; 5,609,010; 5,200,191; 5,459,983; 5,146,730; 5,942,034 describe geltabs and gelcaps and methods and apparatuses for making them. Conventional methods for forming gelcaps are generally performed in a batchwise manner using a number of stand-alone machines operating independently. Such batch processes typically include the unit operations of granulating, drying, blending, compacting (e.g., in a tablet press), gelatin dipping or enrobing, drying, and printing.

Unfortunately, these processes have certain drawbacks. For example, because these systems are batch processes, each of the various apparatuses employed is housed in a separate clean room that must meet FDA standards. This requires a relatively large amount of capital in terms of both space and machinery. A process that would increase and streamline production rates would therefore provide many economic benefits including a reduction in the size of facilities needed to mass-produce pharmaceutical products. Generally, it would be desirable to create a continuous operation process, as opposed to a batch process, for formation of gelcaps and other dosage forms.

Furthermore, gel dipping and drying operations are in general relatively time consuming. Thus, a process that simplifies the gelatin coating operation in particular and reduces drying time would also be advantageous.

Current equipment for making gelcaps and geltabs is designed to produce these forms only according to precise specifications of size and shape. A more versatile method and apparatus, which could be used to produce a variety of dosage forms to deliver pharmaceuticals, nutritionals, and/or confections, would therefore also be advantageous.

Accordingly, applicants have now discovered that a wide variety of dosage forms, including compressed tablets, gelcaps, chewable tablets, liquid fill tablets, high potency dosage forms, and the like, some of which in and of themselves are novel, can be made using unique operating modules. Each operating module performs distinct functions, and therefore may be used as a stand-alone unit to make certain dosage forms. Alternatively, two or more of the same or different operating modules may be linked together to form a continuous process for producing other dosage forms. In essence, a "mix and match" system for the production of dosage forms is provided by the present invention. Preferably, the operating modules may be linked together as desired to operate as a single continuous process.

SUMMARY OF THE INVENTION

The present invention relates to a method of making a coated dosage form by introducing a core into a mold shell and injecting a flowable material under pressure into the mold shell. The mold shell has an interior surface capable of providing a discontinuous coating around said dosage form. For example, the mold shell can have an interior surface with at least one protrusion that extends toward the dosage core. Alternatively, the mold shell has an interior surface with a plurality of protrusions that extend toward and optionally touch the surface of the core. The plurality of protrusions can be an integral and inseparable part of the mold shell. In an alternative embodiment, the core rests on a spring-biased holding mechanism. In one embodiment, the core can be a compressed powder containing a medicant.

The present invention also relates to a method of making a coated dosage form by: a) compressing a powder material into a compressed core in a compression module; b) transferring said compressed core from the compression module to an injection molding module; c) injecting a flowable material into a mold shell having an interior surface capable of providing a discontinuous coating around said compressed core; and d) hardening said flowable material so as to form a discontinuous coating over said compressed core. Advantageously, steps (a) through (d) are linked together such that essentially no interruption occurs between said steps. One or more of said steps can be performed on a continuous basis.

In a further embodiment, steps (a) through (d) are performed simultaneously, such that while coatings are being hardened on a first group of compressed cores in step (d), flowable material is being molded around a second group of compressed cores in step (c), a third group of compressed cores are being transferred to said injection molding module in step (b), and a fourth group of compressed cores are being formed in step (a). In a still further embodiment, step (c) includes the steps of:

(i) injecting into a first mold shell a first flowable material around a first portion of said compressed core; and
(ii) injecting into a second mold shell a second flowable material around a second portion of said compressed core.

Either the first mold shell or the second mold shell or both mold shells have a surface capable of producing a discontinuous coating over at least a portion of said compressed core.

The present invention further relates to a mold shell having a generally global, circular, cylindrical or elliptical shape that is sized for coating a substrate selected from a compressed core for health, particularly human, or medicinal purposes and molded dosage inserts having an interior surface with at least one protrusion extending toward a resting position for said substrate. The present invention further relates to a plate having a plurality of mold shells described above.

The present invention further relates to a dosage form made by the method described herein having at least one opening passing through the coating to expose the compressed core.

The invention also provides compressed cores containing at least about 85 percent by weight of a medicant selected from the group consisting of acetaminophen, ibuprofen, flurbiprofen, ketoprofen, naproxen, diclofenac, aspirin, pseudoephedrine, phenylpropanolamine, chlorpheniramine maleate, dextromethorphan, diphenhydramine, famotidine, loperamide, ranitidine, cimetidine, astemizole, terfenadine, fexofenadine, loratadine, cetirizine, antacids, mixtures thereof and pharmaceutically acceptable salts thereof, and being substantially free of water soluble polymeric binders, the relative standard deviation in weight of said compressed cores being less than about 2%.

The invention also provides compressed cores containing at least about 85 percent by weight of a medicant and being substantially free of hydrated polymers, the relative standard deviation in weight of said compressed cores being less than about 2%, alternatively, the relative standard deviation in weight of said compressed cores is less than about 1%.

The invention also provides a dosage form comprising a substrate having a coating thereon and at least one opening that exposes the substrate, said coating having a thickness of about 100 to about 400 microns; the relative standard deviation in thickness of said coating being less than 30%; wherein said coating is substantially free of humectants. The invention also provides a dosage form comprising a tablet having a coating thereon and at least one opening that exposes the substrate, said coating having a thickness of about 100 to about 400 microns, wherein the relative standard deviation in thickness of said dosage form is not more than about 0.35%; and wherein said coating is substantially free of humectants.

BRIEF DESCRIPTION OF THE DRAWINGS

FIG. 2 is a plan view, partially schematic, of a system for manufacturing dosage forms according to the invention.

FIGS. 14–16 are cross-sectional views of a preferred nozzle system of a center mold assembly.

FIGS. 18–20 are cross-sectional views of the upper mold assembly and the center mold assembly of the injection molding module.

DETAILED DESCRIPTION OF INVENTION

The methods, systems, and apparatuses of this invention can be used to manufacture conventional dosage forms, having a variety of shapes and sizes, as well as novel dosage forms that could not have been manufactured heretofore using conventional systems and methods. In its most general sense, the invention provides an injection molding process for coating dosage forms using a mold shell with an interior surface capable of providing a discontinuous coating around the dosage form. Further, the invention includes the combination of: 1) a compression module for making compressed cores from compressible powders, 2) an injection molding module having the modified interior surface for applying a discontinuous coating to a substrate, and 3) a transfer device for transferring dosage forms from one module to another.

Figure 1:
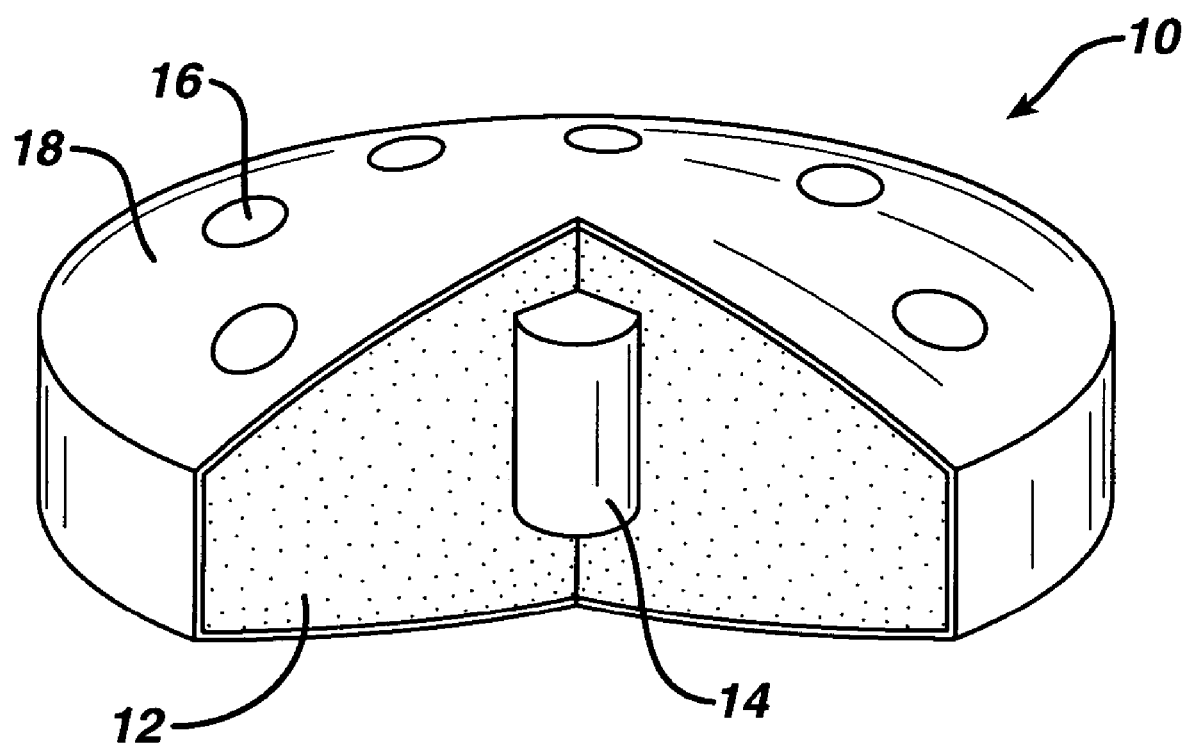
FIG. 1 is an example of a dosage form made according to the invention.
Figure 1A:
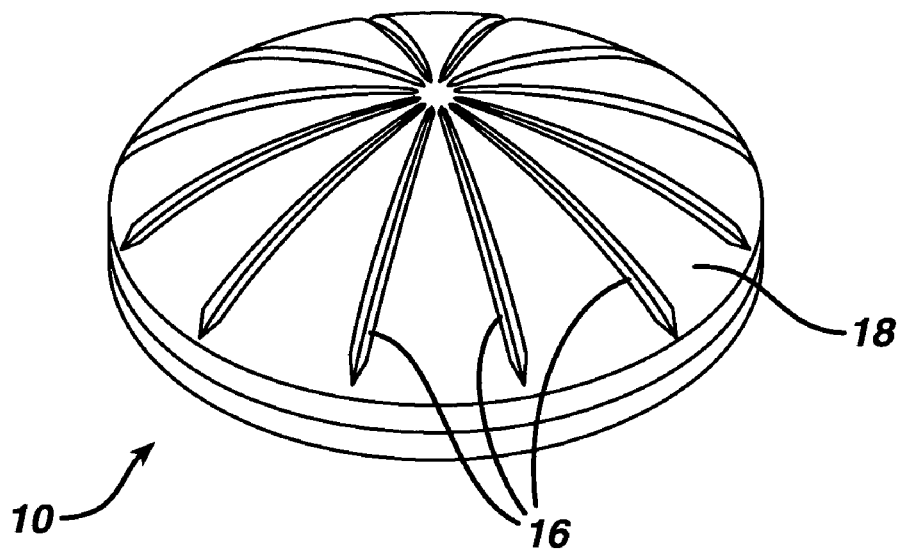
FIGS. 1A, 1B, 1C and 1D illustrate alternative dosage forms.
Figure 1B:
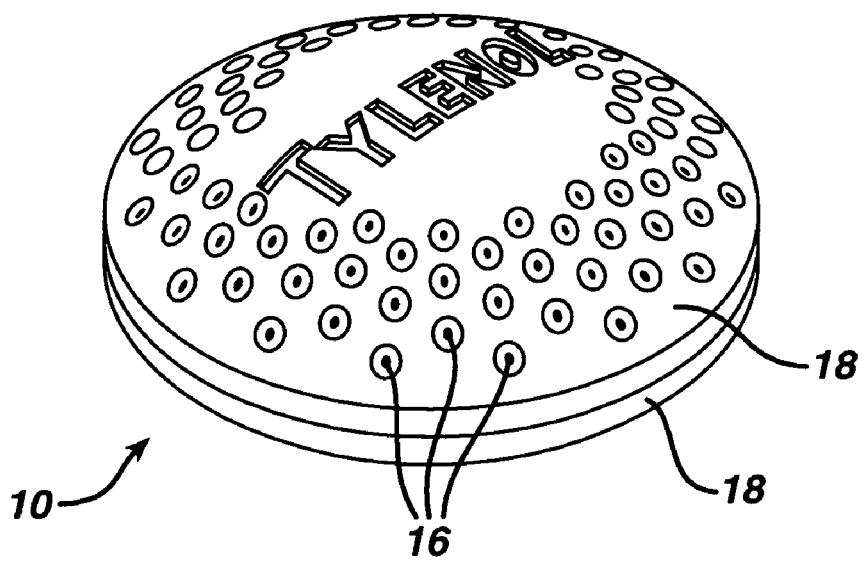
Figure 1C:
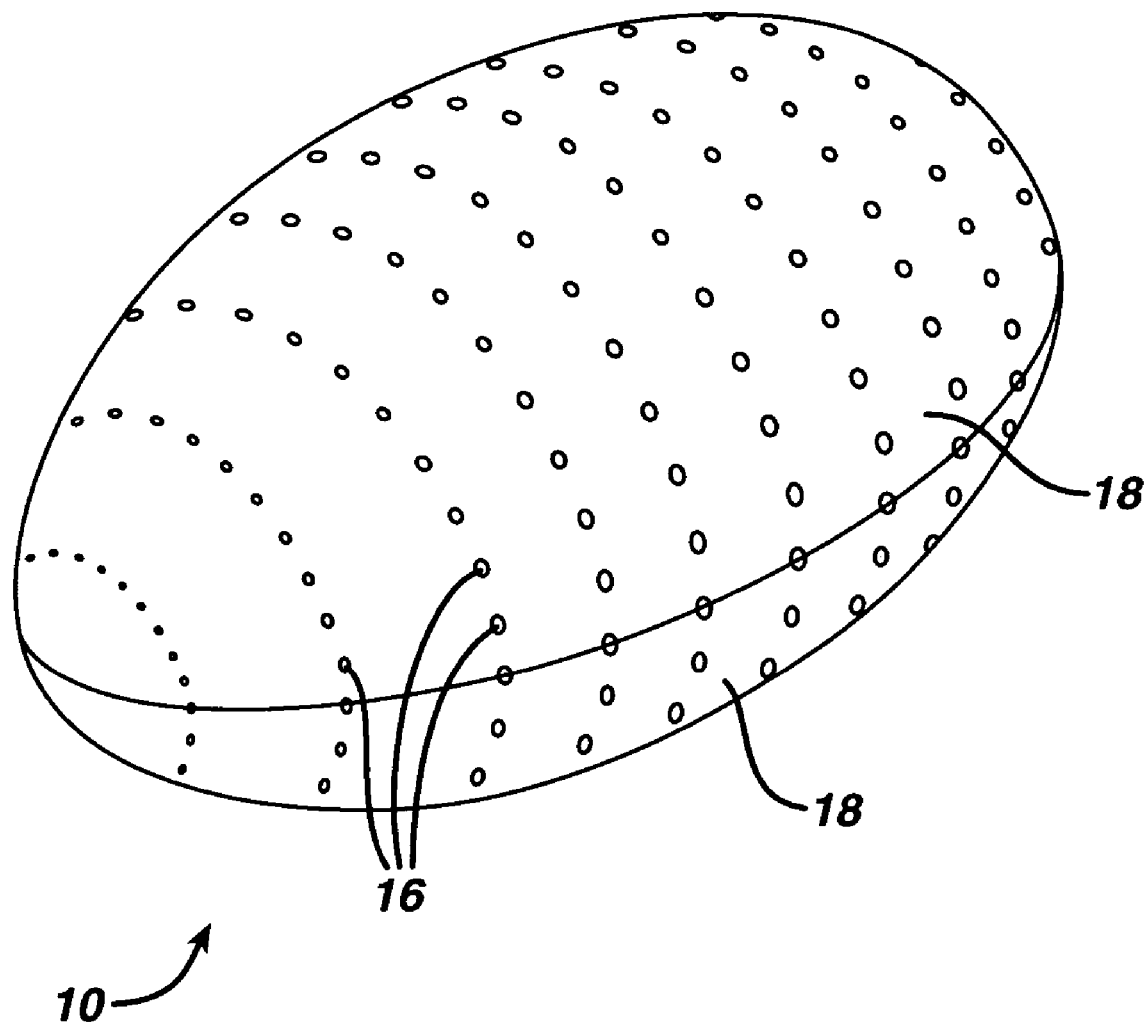
Figure 1D:
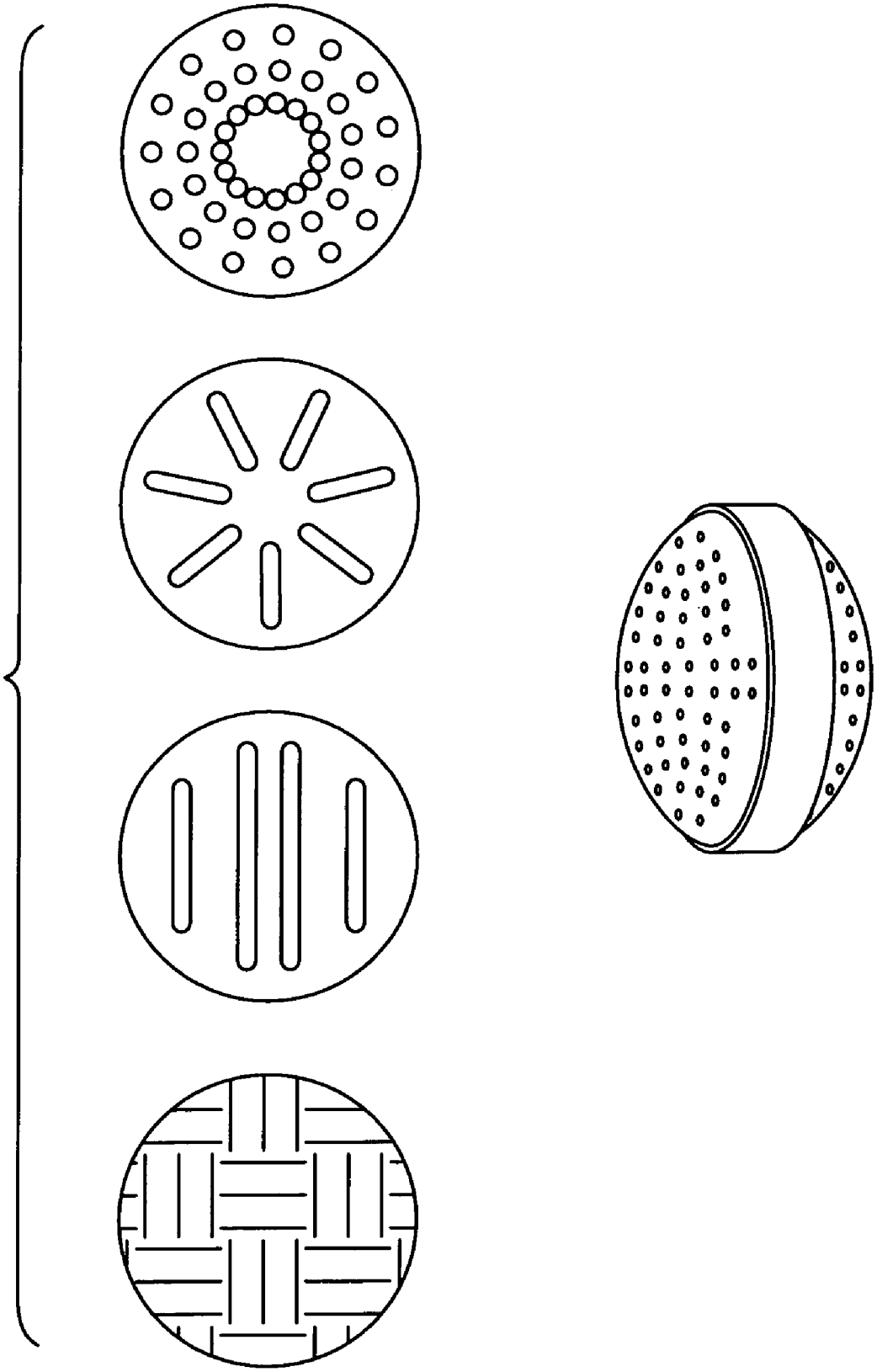

In one embodiment, the inventive process produces a dosage form 10 comprising a molded coating 18 having at least one, preferably a plurality, of openings 16 on the outside surface of a core 12 optionally also containing an insert 14 as shown in FIG. 1. It may be appreciated from FIG. 1 that the coating is discontinuous as indentations or holes or openings (as shown) prevent the coatings from uniformly coating the entire surface.

FIG. 1 depicts a dosage form 10 according to the invention comprising a molded coating 18 having a plurality of openings 16. Openings 16 are shaped as elongated slits, and do not extend all the way through the molded coating 18 to the core (not shown).

FIG. 1 depicts another dosage form according to the invention. The dosage form 10 comprises a core (not shown) having a first molded coating 18a and a second molding coating 18b. Molded coating 18a contains a plurality of openings 16a and 16b. Openings 16a are shaped as dimples, while openings 16b are shaped as letters.

FIG. 1 illustrates another dosage form according to the invention. Dosage form 10 comprises a core (not shown) covered by molded coating 18, which comprises openings 16a and 16b. Openings 16a are shaped as circular holes, while openings 16b are shaped as letters.

Figure 3:
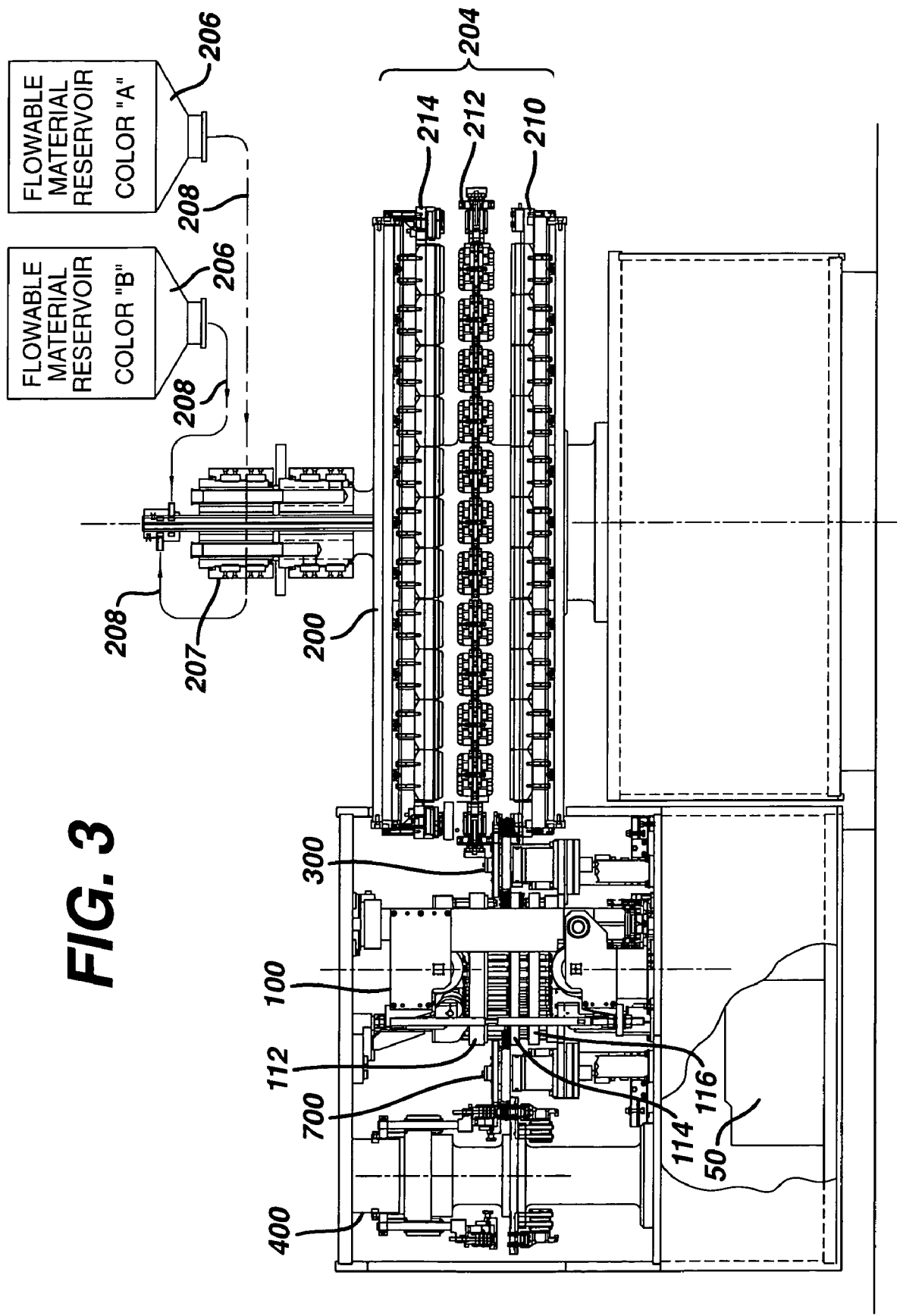
FIG. 3 is an elevational view of the system shown in FIG. 3.

By way of overview, a preferred system 20 comprises an optional compression module 100, an injection molding module 200 and an optional transfer device 300 for transferring a core (optionally made in the compression module 100, or alternately made in a second molding module) to the injection molding module 200 as shown in FIGS. 2 and 3.

In certain preferred embodiments, linkage of the compression module, transfer device, and the injection molding module in this manner results in a continuous, multi-station system. In such embodiments, compression is accomplished in the first module, molding of a coating around the resulting compressed core is performed in the second module, and the transfer device accomplishes transfer of the intermediate dosage form from one module to the other.

In other optional embodiments, the system 20 also includes a thermal setting molding module 400 for forming a molded dosage form, which may comprise the final dosage form or be an insert for incorporation into another dosage form. In a preferred embodiment, the insert comprises a high potency additive. The invention is not limited to the type or nature of insert. Rather, the term insert is used simply to denote a pellet-type component embedded in another dosage form. Such an insert may itself contain a medicant, and retains its shape while being placed within the powder. The insert is inserted into uncompressed powder within compression module 100. After insertion the powder and insert are compressed. The thermal setting molding module 400 can be separate from or part of the compression module 100. If the thermal setting molding module is separate from the compression module 100, a transfer device 700 can be used to transfer the insert from the thermal setting molding module 400 to the compression module 100.

The linked system for creating dosage forms, as well as each individual operating module, provide many processing advantages. The operating modules may be used separately or together, in different sequences, depending on the nature of the dosage form desired. Two or more of the same operating modules may be used in a single process. And although the apparatuses, methods and systems of this invention are described with respect to making dosage forms, it will be appreciated that they can be used to produce non-medicinal products as well. For example, they may be used to make confections or placebos. The molding module can be used with numerous natural and synthetic materials with or without the presence of a medicant. Similarly, the compression module can be used with various powders with or without drug. These examples are provided by way of illustration and not by limitation, and it will be appreciated that the inventions described herein have numerous other applications.

When linked in a continuous process, the operating modules can each be powered individually or jointly. In the preferred embodiment shown in FIGS. 3 and 4, a single motor 50 powers the compression module 100, the injection molding module 200, and the transfer device 300. The motor 50 can be coupled to the compression module 100, the injection molding module 200 and the transfer device 300 by any conventional drive train, such as one comprising gears, gear boxes, line shafts, pulleys, and/or belts. Of course, such a motor or motors can be used to power other equipment in the process, such as the dryer 500 and the like.

As used herein, the term "dosage form" applies to any solid object, semi-solid, or liquid composition designed to contain a specific pre-determined amount (dose) of a certain ingredient, for example an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like.

Preferably the dosage forms of the present invention are considered to be solid, however they may contain liquid or semi-solid components. In a particularly preferred embodiment, the dosage form is an orally administered system for delivering a pharmaceutical active ingredient to the gastrointestinal tract of a human. In another preferred embodiment, the dosage form is an orally administered "placebo" system containing pharmaceutically inactive ingredients, and the dosage form is designed to have the same appearance as a particular pharmaceutically active dosage form, such as may be used for control purposes in clinical studies to test, for example, the safety and efficacy of a particular pharmaceutically active ingredient.

The dosage form of the present invention preferably contains one or more active ingredients. Suitable active ingredients broadly include, for example, pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for H. pylori, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

In one embodiment of the invention, at least one active ingredient may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, at least one active ingredient is selected from analgesics, anti-inflammatories, and antipyretics, e.g. non-steroidal anti-inflammatory drugs (NSAIDs), including a) propionic acid derivatives, e.g. ibuprofen, naproxen, ketoprofen and the like; b) acetic acid derivatives, e.g. indomethacin, diclofenac, sulindac, tolmetin, and the like; c) fenamic acid derivatives, e.g. mefenamic acid, meclofenamic acid, flufenamic acid, and the like; d) biphenylcarbodylic acid derivatives, e.g. diflunisal, flufenisal, and the like; e) oxicams, e.g. piroxicam, sudoxicam, isoxicam, meloxicam, and the like; f) cyclooxygenase-2 (COX-2) selective NSAIDs; and g) pharmaceutically acceptable salts of the foregoing.

In one particular embodiment, at least one active ingredient is selected from propionic acid derivative NSAID, which are pharmaceutically acceptable analgesics/non-steroidal anti-inflammatory drugs having a free —CH(CH$_3$)

COOH or —CH$_2$CH$_2$COOH or a pharmaceutically acceptable salt group, such as —CH(CH$_3$)COO—Na+ or CH$_2$CH$_2$COO—Na+, which are typically attached directly or via a carbonyl functionality to a ring system, preferably an aromatic ring system.

Examples of useful propionic acid derivatives include ibuprofen, naproxen, benoxaprofen, naproxen sodium, fenbufen, flurbiprofen, fenoprofen, fenbuprofen, ketoprofen, indoprofen, pirprofen, carpofen, oxaprofen, pranoprofen, microprofen, tioxaprofen, suprofen, alminoprofen, tiaprofenic acid, fluprofen, bucloxic acid, and pharmaceutically acceptable salts, derivatives, and combinations thereof.

In one embodiment of the invention, the propionic acid derivative is selected from ibuprofen, ketoprofen, flubiprofen, and pharmaceutically acceptable salts and combinations thereof. In another embodiment, the propionic acid derivative is ibuprofen, 2-(4-isobutylphenyl) propionic acid, or a pharmaceutically acceptable salt thereof, such as the arginine, lysine, or histidine salt of ibuprofen. Other pharmaceutically acceptable salts of ibuprofen are described in U.S. Pat. Nos. 4,279,926, 4,873,231, 5,424,075 and 5,510,385, the contents of which are incorporated by reference.

In another particular embodiment of the invention, at least one active ingredient may be an analgesic selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another particular embodiment of the invention, at least one active ingredient may be selected from pseudoephedrine, phenylpropanolamine, chlorpheniramine, dextromethorphan, diphenhydramine, astemizole, terfenadine, fexofenadine, loratadine, desloratadine, cetirizine, mixtures thereof and pharmaceutically acceptable salts, esters, isomers, and mixtures thereof.

In another particular embodiment, at least one active ingredient is an NSAID and/or acetaminophen, and pharmaceutically acceptable salts thereof.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art. Typically, the dosage form comprises at least about 1 weight percent, preferably, the dosage form comprises at least about 5 weight percent, e.g. about 20 weight percent of a combination of one or more active ingredients. In one preferred embodiment, the core comprises a total of at least about 25 weight percent (based on the weight of the core) of one or more active ingredients.

The active ingredient or ingredients may be present in the dosage form in any form. For example, one or more active ingredients may be dispersed at the molecular level, e.g. melted or dissolved, within the dosage form, or may be in the form of particles, which in turn may be coated or uncoated. If an active ingredient is in form of particles, the particles (whether coated or uncoated) typically have an average particle size of about 1–2000 microns. In one preferred embodiment, such particles are crystals having an average particle size of about 1–300 microns. In another preferred embodiment, the particles are granules or pellets having an average particle size of about 50–2000 microns, preferably about 50–1000 microns, most preferably about 100–800 microns.

In certain embodiments, at least a portion of one or more active ingredients may be optionally coated with a release-modifying coating, as known in the art. This advantageously provides an additional tool for modifying the release profile of active ingredient from the dosage form. For example, the core may contain coated particles of one or more active ingredients, in which the particle coating confers a release modifying function, as is well known in the art. Examples of suitable release modifying coatings for particles are described in U.S. Pat. Nos. 4,173,626; 4,863,742; 4,980,170; 4,984,240; 5,286,497; 5,912,013; 6,270,805; and 6,322,819. Commercially available modified release coated active particles may also be employed. Accordingly, all or a portion of one or more active ingredients in the core may be coated with a release-modifying material.

In embodiments in which it is desired for at least one active ingredient to be absorbed into the systemic circulation of an animal, the active ingredient or ingredients are preferably capable of dissolution upon contact with a dissolution medium such as water, gastric fluid, intestinal fluid or the like.

In one embodiment, the dissolution characteristics of at least one active ingredient meets USP specifications for immediate release tablets containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19–20 and 856 (1999). In embodiments in which at least one active ingredient is released immediately, the immediately released active ingredient is preferably contained in the shell or on the surface of the shell, e.g. in a further coating surrounding at least a portion of the shell.

In another embodiment, the dissolution characteristics of one or more active ingredients are modified: e.g. controlled, sustained, extended, retarded, prolonged, delayed and the like. In a preferred embodiment in which one or more active ingredients are released in a modified manner, the modified release active or actives are preferably contained in the core. As used herein, the term "modified release" means the release of an active ingredient from a dosage form or a portion thereof in other than an immediate release fashion, i.e., other than immediately upon contact of the dosage form or portion thereof with a liquid medium. As known in the art, types of modified release include delayed or controlled. Types of controlled release include prolonged, sustained, extended, retarded, and the like. Modified release profiles that incorporate a delayed release feature include pulsatile, repeat action, and the like. As is also known in the art, suitable mechanisms for achieving modified release of an active ingredient include diffusion, erosion, surface area control via geometry and/or impermeable or semi-permeable barriers, and other known mechanisms.

In certain embodiments, the dosage form of the present invention comprises a core and a shell. The core may be any solid form. The core can be prepared by any suitable method, including for example compression or molding. Suitable method of manufacturing solid cores are well known in the art such as the techniques on pages 1576–1607 of Remington's Pharmaceutical Sciences, Mack Publishing Company (Fifteenth edition), 1975 the text of which is hereby incorporated by reference.

Additionally, the cores are, in one embodiment, provided with a precoat sealant "subcoat" that covers the entire core before incorporation of the outer visible coating (shell). The precoat sealant can be colored, opaque or transparent. The use of subcoatings is well known in the art and disclosed in, for example, U.S. Pat. No. 5,234,099, which is incorporated by reference herein. Any composition suitable for film-coating a tablet may be used as a subcoating according to the present invention. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein.

Additional suitable subcoatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as Polysorbate-80, sodium lauryl sulfate and dioctyl-sodium sulfosuccinate; polycarbohydrates, pigments, and opacifiers.

In one embodiment, the subcoating comprises from about 2 percent to about 8 percent, e.g. from about 4 percent to about 6 percent of a water-soluble cellulose ether and from about 0.1 percent to about 1 percent, castor oil, as disclosed in detail in U.S. Pat. No. 5,658,589, which is incorporated by reference herein. In another embodiment, the subcoating comprises from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400. The dried subcoating typically is present in an amount, based upon the dry weight of the core, from about 0 percent to about 5 percent. As used herein, "core" refers to a material that is at least partially enveloped or surrounded by another material. Preferably, the core is a self-contained unitary object, such as a tablet or capsule. Typically, the core comprises a solid, for example, the core may be a compressed or molded tablet, hard or soft capsule, suppository, or a confectionery form such as a lozenge, nougat, caramel, fondant, or fat based composition. In certain other embodiments, the core or a portion thereof may be in the form of a semi-solid or a liquid in the finished dosage form. For example the core may comprise a liquid filled capsule, or a semisolid fondant material. In embodiments in which the core comprises a flowable component, such as a plurality of granules or particles, or a liquid, the core preferably additionally comprises an enveloping component, such as a capsule shell, or a coating, for containing the flowable material. In certain particular embodiments in which the core comprises an enveloping component, the shell or shell portions of the present invention are in direct contact with the enveloping component of the core, which separates the shell from the flowable component of the core.

The core of the present invention, depending on the method by which it is made, typically comprises, in addition to the active ingredient, a variety of excipients (inactive ingredients which may be useful for conferring desired physical properties to the core or dosage form). In embodiments in which the core is prepared by compression, suitable excipients for compression include fillers, binders, disintegrants, lubricants, glidants, and the like, as well as release-modifying compressible excipients, as are well known in the art. Suitable release-modifying compressible excipients for making the core, or a portion thereof, by compression include swellable erodible hydrophilic materials, insoluble edible materials, pH-dependent polymers, and the like.

In one embodiment the core is a compressed tablet having a hardness from about 2 to about 30 kp/cm$^2$, e.g. from about 6 to about 25 kp/cm$^2$. "Hardness" is a term used in the art to describe the diametral breaking strength of either the core or the coated solid dosage form as measured by conventional pharmaceutical hardness testing equipment, such as a Schleuniger Hardness Tester. In order to compare values across different size tablets, the breaking strength must be normalized for the area of the break. This normalized value, expressed in kp/cm$^2$, is sometimes referred in the art as tablet tensile strength. A general discussion of tablet hardness testing is found in Leiberman et al., *Pharmaceutical Dosage Forms-Tablets*, Volume 2, 2$^{nd}$ ed., Marcel Dekker Inc., 1990, pp. 213–217, 327–329.

The core may have one of a variety of different shapes. For example, the core may be shaped as a polyhedron, such as a cube, pyramid, prism, or the like; or may have the geometry of a space figure with some non-flat faces, such as a cone, truncated cone, cylinder, sphere, torus, or the like. In certain embodiments, a core has one or more major faces. For example, in embodiments wherein a core is a compressed tablet, the core surface typically has two opposing major faces formed by contact with the upper and lower punch faces in the compression machine. In such embodiments the core surface typically further comprises a "bellyband" located between the two major faces, and formed by contact with the mold shell walls in the compression machine. A core may also comprise a multilayer tablet.

Exemplary core shapes that may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference) as follows (the tablet shape corresponds inversely to the shape of the compression tooling):

1. Shallow Concave.
2. Standard Concave.
3. Deep Concave.
4. Extra Deep Concave.
5. Modified Ball Concave.
6. Standard Concave Bisect.
7. Standard Concave Double Bisect.
8. Standard Concave European Bisect.
9. Standard Concave Partial Bisect.
10. Double Radius.
11. Bevel & Concave.
12. Flat Plain.
13. Flat-Faced-Beveled Edge (F.F.B.E.).
14. F.F.B.E. Bisect.
15. F.F.B.E. Double Bisect.
16. Ring.
17. Dimple.
18. Ellipse.
19. Oval.
20. Capsule.
21. Rectangle.
22. Square.
23. Triangle.
24. Hexagon.
25. Pentagon.
26. Octagon.
27. Diamond.

Figure 8:
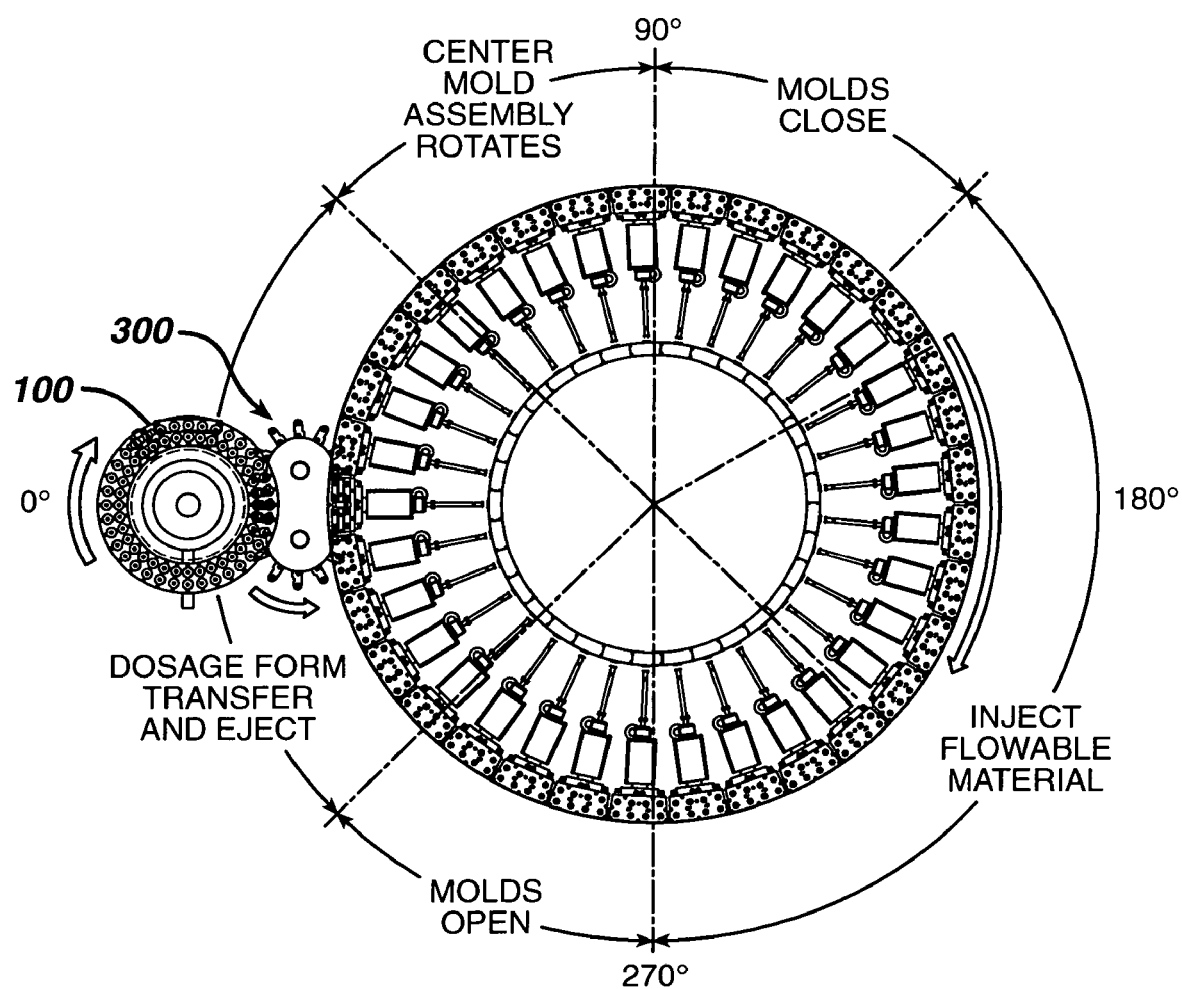
FIG. 8 illustrates process steps for one embodiment of the invention.

28. Arrowhead.
29. Bullet.
30. Shallow Concave.
31. Standard Concave.
32. Deep Concave.
33. Extra Deep Concave.
34. Modified Ball Concave.
35. Standard Concave Bisect.
36. Standard Concave Double Bisect.
37. Standard Concave European Bisect.
38. Standard Concave Partial Bisect.
39. Double Radius.
40. Bevel & Concave.
41. Flat Plain.
42. Flat-Faced-Beveled Edge (F.F.B.E.).
43. F.F.B.E. Bisect.
44. F.F.B.E. Double Bisect.
45. Ring.
46. Dimple.
47. Ellipse.
48. Oval.
49. Capsule.
50. Rectangle.
51. Square.
52. Triangle.
53. Hexagon.
54. Pentagon.
55. Octagon.
56. Diamond.
57. Arrowhead.
58. Bullet.
59. Barrel.
60. Half Moon.
61. Shield.
62. Heart.
63. Almond.
64. House/Home Plate.
65. Parallelogram.
66. Trapezoid.
67. FIG. 8/Bar Bell.
68. Bow Tie.
69. Uneven Triangle.

A shell surrounds the cores. The shell comprises one or more openings or indentations therein. In certain embodiments, the opening or openings provide a passageway for communication between the core and the exterior of the dosage form. The openings may extend completely through the thickness of the shell to contact the core, or only partially through the shell. Each opening may have dimensions, e.g., length, width, or diameter, in the range of about 0.1% to about 100%, of the diameter of the dosage form, or of any dimension (e.g. diameter, length, or width) of a major face of the dosage form. The diameter or width of each opening is preferably from about 0.5% to about 5% of the diameter of the dosage form, or of any dimension (e.g. diameter, length, or width) of a major face of the dosage form. In certain embodiments the diameter or width of the openings may range from about 200 to about 2000 microns. The length of the openings may range from about 1% to about 100% of the diameter of the dosage form, or of the diameter of a major face of the dosage form. In certain particular embodiments, the length or diameter of a major face of the dosage form is from about 10,000 to about 20,000 microns. In one particular embodiment, the length of the openings is from about 100 to about 20,000 microns. The depth of the openings is typically from about 75% to about 100% of the thickness of the shell at the location of the openings. In certain embodiments, the thickness of the shell at the location of the openings typically ranges from about 20 to about 800 microns, e.g. from about 100 to about 400 microns. In one particular embodiment, the depth of the openings is from about 75 to about 400 microns. If a plurality of openings is present, they are typically spaced from one another by at least about one half, e.g. at least about one, times the smallest dimension of the smallest opening. The openings may have a variety of shapes, or be arranged in a variety of different patterns, and may have similar or different sizes. In one embodiment, the size of the openings is small enough to prevent the core from being tasted, yet the number of openings is large enough to provide communication between a certain percentage of surface area of the core and the exterior of the dosage form.

The shell thickness at various locations may be measured using a microscope, for example, an environmental scanning electron microscope, model XL 30 ESEM LaB6, Philips Electronic Instruments Company, Mahwah, Wis. The shell thickness is measured at 6 different locations on a single dosage form. The relative standard deviation (RSD) is calculated as the sample standard deviation, divided by the mean, times 100 as known in the art (i.e. the RSD is the standard deviation expressed as a percentage of the mean). The RSD in shell thickness provides an indication of the variation in the thickness of the shell on a single dosage form. In certain optional embodiments of the invention, the relative standard deviation in shell thickness is less than about 40%, e.g. less than about 30%, or less than about 20%.

The shell may be substantially unitary and continuous with the exception of the openings therein, or the shell may comprise multiple portions, e.g. a first shell portion and a second shell portion. In certain embodiments the shell or shell portions are in direct contact with the core. In certain other embodiments, the shell or shell portions are in direct contact with a subcoating that substantially surrounds the core. In embodiments in which the shell comprises a first and second shell portion, at least a first shell portion comprises openings therein.

In certain embodiments the first shell portion and second shell portion are compositionally different. As used herein, the term "compositionally different" means having features that are readily distinguishable by qualitative or quantitative chemical analysis, physical testing, or visual observation. For example, the first and second shell portions may contain different ingredients, or different levels of the same ingredients, or the first and second shell portions may have different physical or chemical properties, different functional properties, or be visually distinct. Examples of physical or chemical properties that may be different include hydrophylicity, hydrophobicity, hygroscopicity, elasticity, plasticity, tensile strength, crystallinity, and density. Examples of functional properties which may be different include rate and/or extent of dissolution of the material itself or of an active ingredient therefrom, rate of disintegration of the material, permeability to active ingredients, permeability to water or aqueous media, and the like. Examples of visual distinctions include size, shape, topography, or other geometric features, color, hue, opacity, and gloss.

In one embodiment, the dosage form of the invention comprises: a) a core containing an active ingredient; b) an optional subcoating that substantially covers the core; and c) a shell comprising first and second shell portions residing on the surface of the subcoating, the first shell portion comprising one or more openings, and the first shell portion being readily soluble in gastrointestinal fluids. As used herein, "substantially covers" shall mean at least about 95 percent of the surface area of the core is covered by the subcoating.

In one embodiment, the dosage form has a subcoating that is transparent such that the underlying core is visible through the one or more openings provided in the molded coating. Alternatively, the subcoating has the appearance of being translucent or opaque. Colorants, such as pigments, or coloring agents, such as dyes, can be used to modify the coloristic properties of the subcoating. The thickness of the subcoat would be expected to influence the degree of opacity, as well as the timing for dissolution and/or disintegration of the molded coating.

In certain other embodiments, the apparatus and processes described herein can produce a molded dosage form per se.

Figure 4:
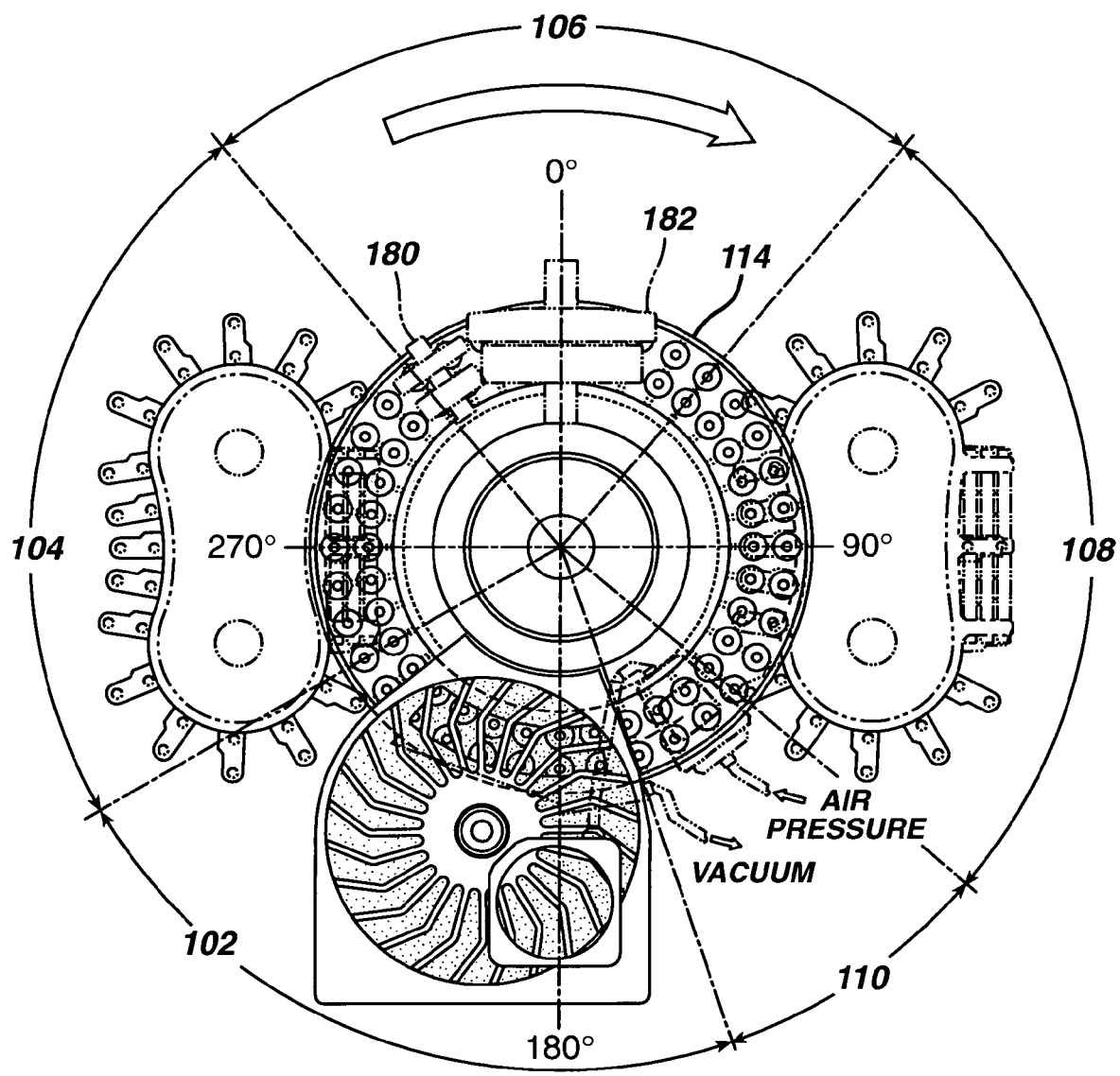
FIG. 4 is top view of a portion of the compression module.

FIG. 4 generally depicts the preferred compression module 100. Other compression systems are suitable for use herein, particularly when a non-continuous process or system is employed. For example, the compressed cores can be prepared in a separate system and then manually delivered to the injection molding module. Of course, such a system lacks the productivity advantages of the preferred system described herein. The remainder of the description will be directed to the preferred system. The preferred compression module 100 is a rotary device that performs the following functions: feeding powder to a cavity, compacting the powder into a compressed core and then ejecting the compressed core. When the compression module is used in conjunction with the injection molding module 200, upon ejection from the compression module the compressed core may be transferred to the molding module either directly or through the use of a transfer device, such as transfer device 300 described below. Optionally, an insert formed by another apparatus, such as the thermal setting molding module 400 described below, can be inserted into the powder in the compression module before the powder is compressed into the compressed core.

In order to accomplish these functions the compression module 100 preferably has a plurality of zones or stations, as shown schematically in FIG. 4, including a fill zone 102, an insertion zone 104, a compression zone 106, an ejection zone 108 and a purge zone 110. Thus, within a single rotation of the compression module 100 each of these functions are accomplished and further rotation of the compression module 100 repeats the cycle. The particulars of the preferred compression module are known and described in Ser. No. 09/966939, filed Sep. 28, 2001, now U.S. Pat. No. 6,837,696, which is incorporated herein by reference.

The rotary portion of the compression module generally includes an upper rotor, a circular die table, a lower rotor, a plurality of upper and lower punches, an upper cam, a lower cam, and a plurality of dies. The upper rotor 112, die table 114 and lower rotor 116 are rotatably mounted about a common shaft 101 shown in FIG. 2.

Each of the rotors and the die table include a plurality of cavities that are disposed along the circumferences of the rotors and die table. Preferably, there are two circular rows of cavities on each rotor. The cavities of each rotor are aligned with a cavity in each of the other rotors and the die table. There are likewise preferably two circular rows of upper punches and two circular rows of lower punches.

Conventional rotary tablet presses are of a single row design and contain one powder feed zone, one compression zone and one ejection zone. This is generally referred to as a single sided press since tablets are ejected from one side thereof. Presses offering a higher output version of the single row tablet press employing two powder feed zones, two tablet compression zones and two tablet ejection zones are commercially available. These presses are typically twice the diameter of the single sided version, have more punches and dies, and eject tablets from two sides thereof. They are referred to as double-sided presses.

In a preferred embodiment of the invention the compression module described herein is constructed with two concentric rows of punches and dies as shown in FIG. 4. This double row construction provides for an output equivalent to two single side presses, yet fits into a small, compact space roughly equal to the space occupied by one conventional single sided press. This also provides a simplified construction by using a single fill zone 102, a single compression zone 106, and a single ejection zone 108. A single ejection zone 108 is particularly advantageous in the linked process of the invention, because the complexity of multiple transfer devices 300, 700 having double sided construction is avoided. Of course, a compression module with one row or more than two rows can also be constructed.

The upper punches extend from above the cavities in the upper rotor through the cavities in the upper rotor and, depending on their position, either proximal to or within the cavities of the die table 114. Similarly, the lower punches extend from beneath the cavities in the lower rotor and into the cavities in the die table.

Disposed within each of the cavities of the die table is a die. Preferably, the dies are metallic, but any suitable material will suffice. Each die may be retained by any of a variety of fastening techniques within the respective cavity of the die table 114. For example, the dies may be shaped so as to have a flange that rests on a seating surface formed in the die table 114 and a pair of o-rings and grooves.

Each die comprises a die cavity for receiving the upper and lower punches. The die cavities and the lower punches that extend a distance into the die cavities define the volume of powder to be formed into the compressed core and hence the dosage amount. Thus, the size of die cavity and the degree of insertion of the punches into the die cavities can be appropriately selected or adjusted to obtain the proper dosage.

Powder is fed into the die cavities in the fill zone 102. The powder may preferably consist of an active ingredient dispersed throughout a matrix containing various excipients, such as binders, disintegrants, lubricants, fillers and the like, as is conventional, or other particulate material of a medicinal or non-medicinal nature, such as inactive placebo blends for tableting, confectionery blends, and the like.

Suitable excipients for compressed cores include fillers, which include water-soluble compressible carbohydrates such as dextrose, sucrose, mannitol, sorbitol, maltitol, xylitol, lactose, and mixtures thereof, water insoluble plastically deforming materials such as microcrystalline cellulose or other cellulosic derivatives, water-insoluble brittle fracture materials such as dicalcium phosphate, tricalcium phosphate, and the like; other conventional dry binders such as polyvinyl pyrrolidone, hydroxypropylmethylcellulose, and the like; sweeteners such as aspartame, acesulfame potassium, sucralose, and saccharin; lubricants, such as magnesium stearate, stearic acid, talc, and waxes; and glidants, such as colloidal silicon dioxide. The mixture may also incorporate pharmaceutically acceptable adjuvants, including, for example, preservatives, flavors, antioxidants, surfactants, and coloring agents. In one embodiment, the powder is substantially free of water-soluble polymeric binders and hydrated polymers.

After the punches leave the fill zone 102 they enter the insertion zone 104. In this zone the lower punches may retract slightly to allow for an optional insert to be embedded into the soft uncompressed powder in the die cavity via a transfer device 700.

After continued rotation and before entering the compression zone 106, the upper punch is pushed into the die cavity by a cam track. Following this, the upper and lower punches engage the first stage rollers 180 where force is applied to the powder via the first stage rollers. After this initial compression event, the punches enter the second stage rollers 182. The second stage rollers drive the punches into the die cavity to further compress the powder into the desired compressed core. Once past the compression zone the upper punches retract from the die cavity and the lower punches begin to move upward prior to entering the ejection zone 108.

Following the formation of the compressed core in the compression zone 106, the respective die cavity rotates to ejection zone 108 as shown in FIG. 4. The upper punches move upward due to the slope of the cam tracks. The lower punches move upward and into the die cavities until eventually the lower punches eject the compressed core out of the die cavity and optionally into a transfer device 300 as shown in FIG. 3. In the purge zone 110, excess powder is removed from the filters after the compressed core has been ejected from the die cavities by blowing air through or placing suction pressure.

The injection molding module 200 generally includes a rotor 202, as shown in FIGS. 2 and 3, around which a plurality of mold units 204 are disposed. As the rotor 202 revolves, the mold units 204 receive compressed cores, preferably from a transfer device such as transfer device 300. However, as noted earlier, the compressed cores can be delivered via manual transfer. Next, flowable material is injected into the mold units to coat the compressed cores. After the compressed cores have been coated, the coating may be further hardened or dried if required. They may be hardened within the mold units or they may be transferred to another device such as a dryer. Continued revolution of the rotor 202 repeats the cycle for each mold unit.

The injection molding module 200 includes at least one reservoir 206 containing the flowable material, as shown in FIG. 3. There may be a single reservoir for each mold unit, one reservoir for all the mold units, or multiple reservoirs that serve multiple mold units. In a preferred embodiment, flowable material of two different colors is used to make the coating, and there are two reservoirs 206, one for each color. The reservoirs 206 may be mounted to the rotor 202 such that they rotate with the rotor 202, or be stationary and connected to the rotor via a rotary union 207 as shown in FIG. 3. The reservoirs 206 can be heated to assist the flowable material in flowing. The temperature to which the flowable material should be heated of course depends on the nature of the flowable material. Any suitable heating means may be used, such as an electric (induction or resistance) heater or fluid heat transfer media. Any suitable tubing 208 may be used to connect the reservoirs 206 to the mold unit 204. In a preferred embodiment, tubing 208 extends through each of the shafts 213 for each of the center mold assemblies 212.

Figure 5:
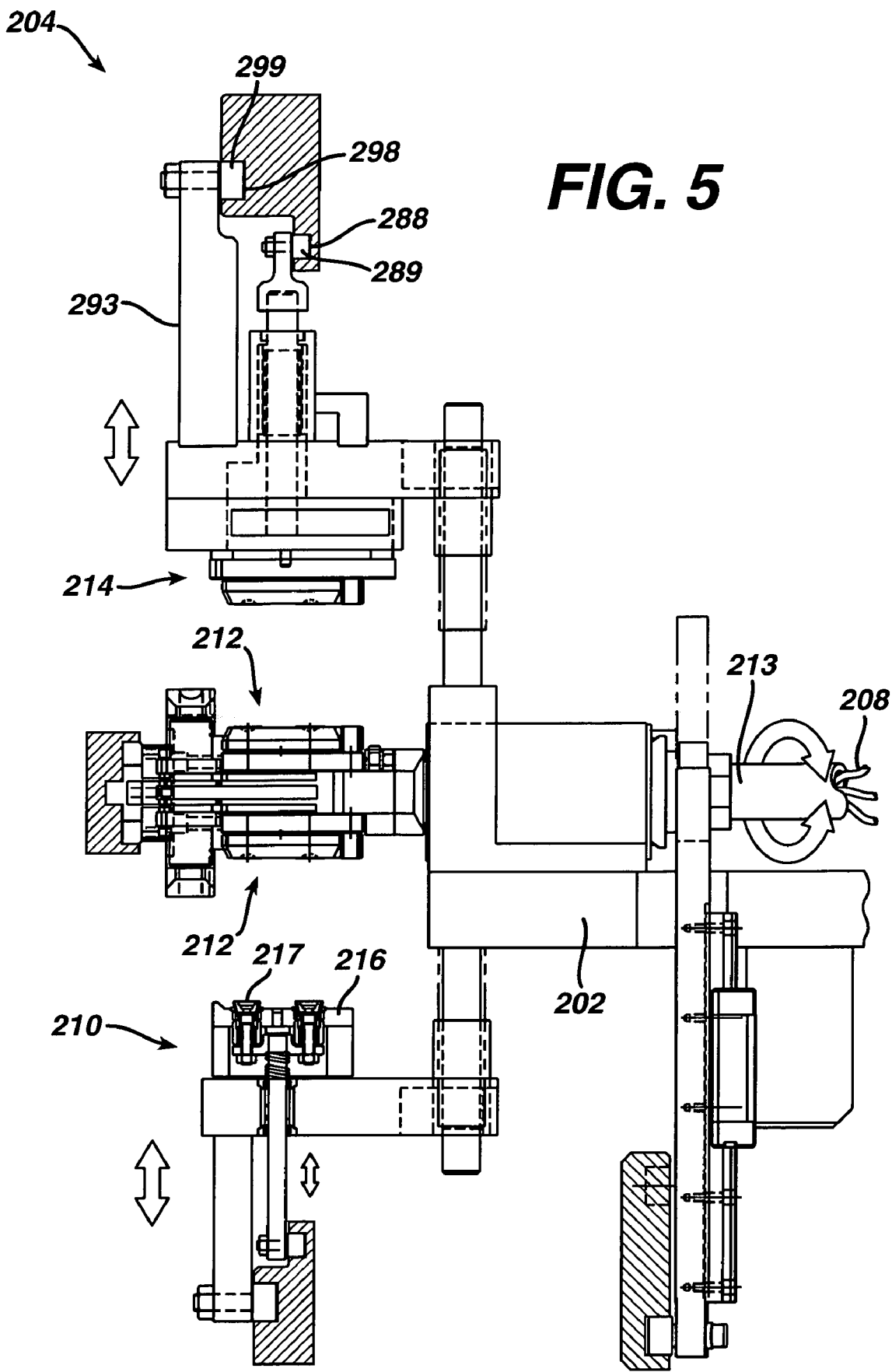
FIG. 5 is a cross-section of an injection molding module.

A preferred embodiment of a mold unit 204 is shown in FIG. 5. The mold unit 204 includes a lower retainer 210, an upper mold assembly 214, and a center mold assembly 212. Each lower retainer 210, center mold assembly 212, and upper mold assembly 214 are mounted to the rotor 202 by any suitable means, including but not limited to mechanical fasteners. Although FIG. 5 depicts a single mold unit 204 all of the other mold units 204 are similar. The lower retainer 210 and the upper mold assembly 214 are mounted so that they can move vertically with respect to the center mold assembly 212. The center mold assembly 212 is preferably rotatably mounted to the rotor 202 such that it may rotate 180 degrees.

The lower retainer 210 is mounted to the rotor 202 as shown in FIG. 5 in any suitable fashion and comprises a plate 216 and a dosage form holder 217. Each dosage form holder can be connected to the plate by any one of a variety of fastening techniques including without limitation snap rings and groves, nuts and bolts, adhesives and mechanical fasteners. The lower retainer preferably has a total of eight dosage form holders.

Figure 6:
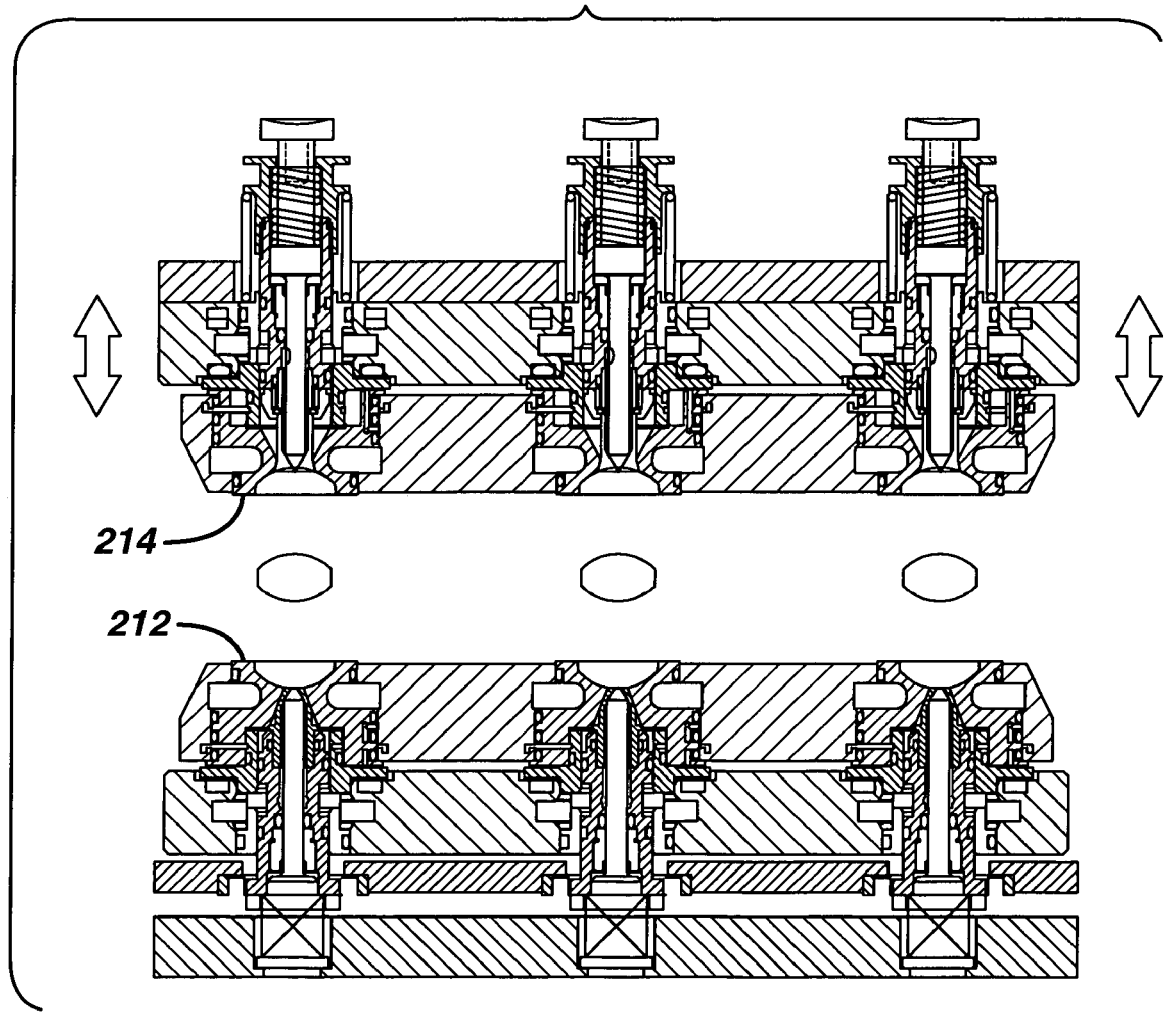
FIGS. 6 and 7 illustrate phases of operation for the injection molding module.
Figure 7:
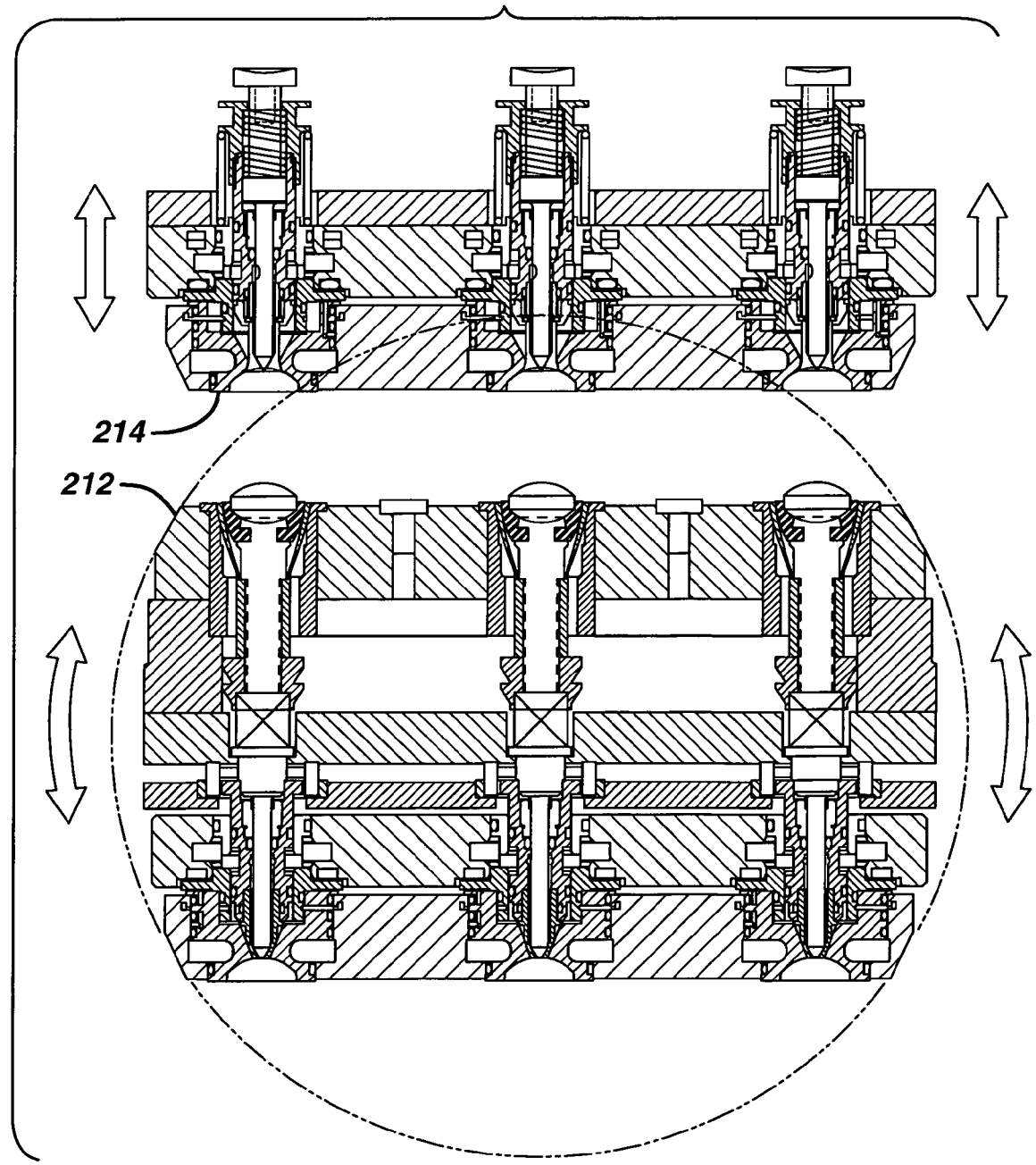

FIG. 6 is a section through one of the mold units. At the beginning of the cycle, the upper mold assembly 214 and the center mold assembly 212 are in the open position. As the rotor continues to revolve the mold assemblies close to form a mold cavity. After the mold assemblies close, hot flowable material is injected from the upper mold assembly, the center mold assembly, or both into the mold cavity. After the flowable material hardens, the mold assemblies open. Upon further revolution of the rotor, the finished molded dosage forms are ejected thus completing one full revolution of the rotor. FIG. 7 is a section through one of the mold units showing upper mold assembly 214 and center mold assembly 212. Note that the center mold assembly 212 in this embodiment is capable of rotation about its axis.

At the beginning of the molding cycle, the mold assemblies are in the open position. Center mold assembly 212 has received a compressed core, for example from a compression module according to the invention transferred via a transfer device also according to the invention. As the rotor continues to revolve, the upper mold assembly 214 closes against center mold assembly 212. Next, flowable material is injected into the mold cavity created by union of the mold assemblies to apply a shell to the first half of the compressed core. The flowable material is cooled in the mold cavity. The mold assemblies open with the half coated compressed cores remaining in the upper mold assembly 214. Upon further revolution of the rotor, the center mold assembly rotates 180 degrees. As the rotor moves past 180 degrees the mold assemblies again close and the uncoated half of the compressed core is covered with flowable material. The mold assemblies again open and the coated compressed core is ejected from the injection molding module.

FIG. 8 depicts the sequence of steps for using a preferred embodiment of the injection molding module to form a coating over a compressed core. In this embodiment, part of a compressed core is coated in the mold cavity created by union of the lower retainer and the center mold assembly 212 during revolution of the rotor between 0 and 360 degrees. Simultaneously, the remainder of a second compressed core, the first part of which has already been coated during a previous revolution of the rotor, is coated in the mold cavity created by the union of the center mold assembly and the upper mold assembly 214. Compressed cores transit through the injection molding module in a helix, receiving partial coatings during a first full rotation of the rotor, and then the remainder of their coatings during a second full rotation of the rotor. Compressed cores are therefore retained in the injection molding module for two revolutions of the rotor (720 degrees) prior to being ejected as finished products.

Figure 9:
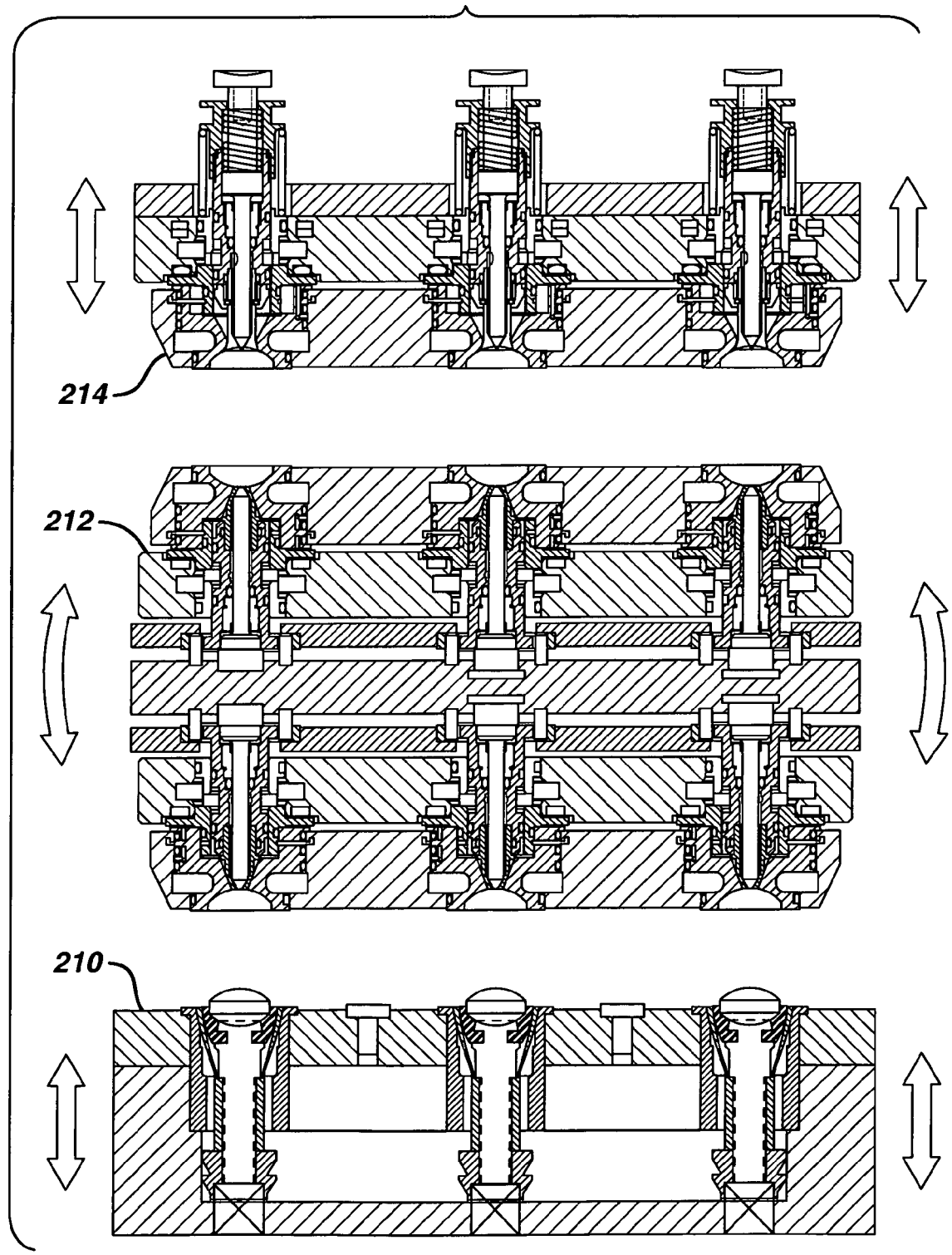
FIGS. 9–11 illustrate a preferred process for an injection molding module.
Figure 10:
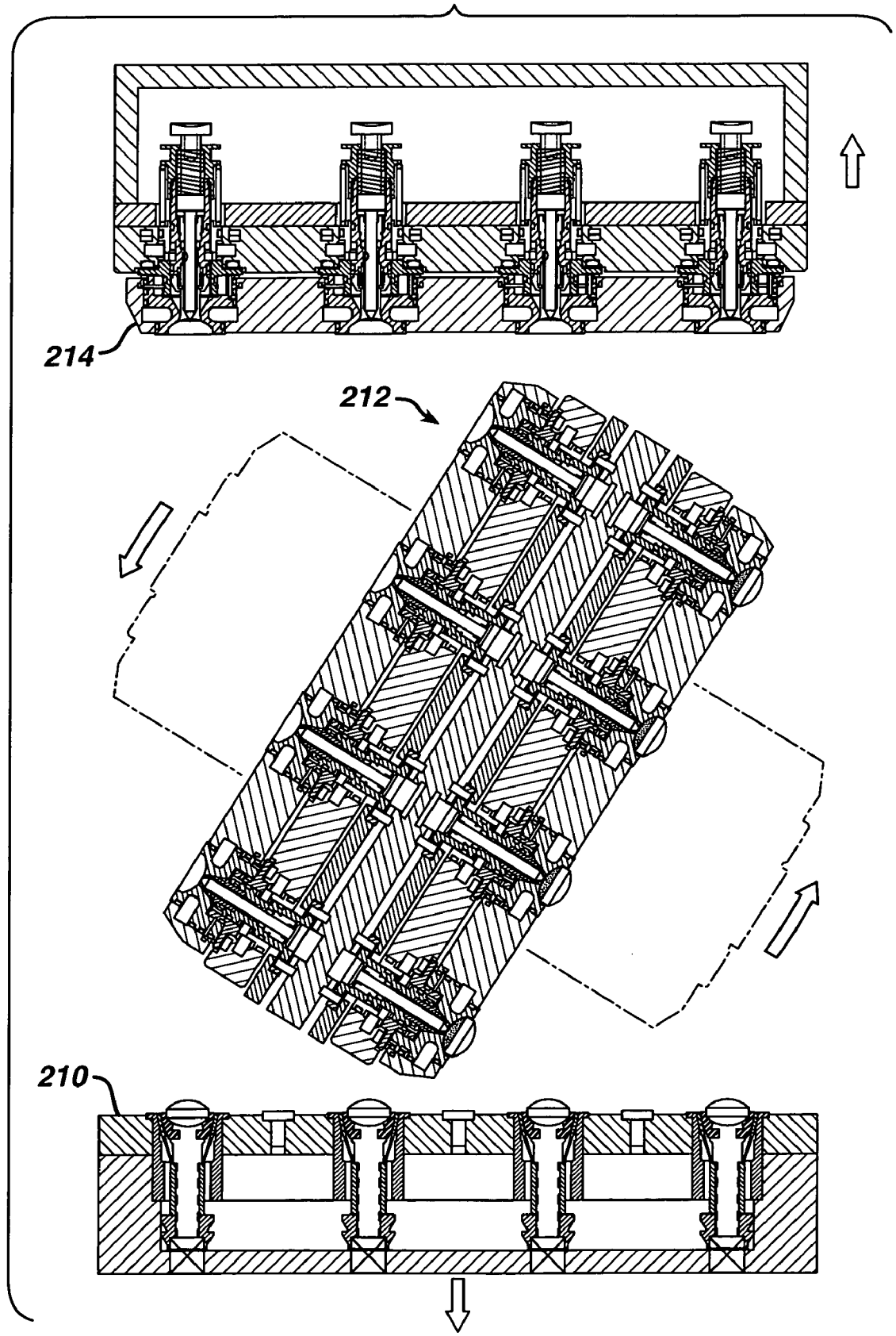

FIG. 9 is a section through one of the mold units. At the beginning of the cycle (0 degrees rotation of the rotor) the mold units are in the open position. The lower mold assembly 210 receives an uncoated compressed core, for example from a compression module 100 via a transfer device 300. In the next step illustrated by FIG. 10, upon rotation of the rotor the center mold assembly 212 rotates 180 degrees about its axis, which is radial to the rotor. This presents the partially coated compressed core to the upper mold assembly 214, which is empty. The partially coated compressed core is then disposed between the upper and center mold assemblies 212, 214. As the rotor continues to rotate, the mold units close. The lower retainer 210 and center mold assembly 212 create a seal around the uncoated compressed core.

Flowable material is injected into the mold cavity created between the lower retainer 210 and the center mold assembly 212 over the uncoated compressed core to cover a part thereof. In a preferred embodiment, the flowable material coats about half of the uncoated compressed core, preferably the top half. Simultaneously with the mating of the lower retainer 210 and the center mold assembly 212, the center 212 and upper 214 mold assemblies mate to create seals around the partially coated compressed core. Flowable material is injected through the upper mold assembly 214 into the mold cavity created by the center mold assembly and the upper mold assembly to coat the remaining portion of the partially coated compressed core, the top portion. The lower retainer 210 and upper mold assembly 214 are mated with the center mold assembly 212 simultaneously. Accordingly, when an uncoated compressed core is being partially coated between the lower retainer 210 and the center mold assembly 212, the remainder of a partially coated compressed core is being coated between the center 212 and upper mold assemblies 214. See FIG. 10.

Following this, the lower retainer and the mold assemblies separate. The fully coated compressed core is retained in the upper mold assembly 214. The partially coated compressed core is retained in the center mold assembly 214. The fully coated compressed core is then ejected from the upper mold assembly 214 as shown schematically in FIG. 11. Following this, an uncoated compressed core is transferred to the lower retainer 210, such that the lower retainer 210, center mold assembly 212, and upper mold assembly 214 return to the position of FIG. 9. The process then repeats itself.

In the preferred embodiment shown, each mold unit can coat eight compressed cores. Of course, the mold units can be constructed to coat any number of compressed cores. Additionally and preferably, the compressed cores are coated with two different colored flowable materials. Any colors can be used. Alternatively, only a portion of the compressed core may be coated while the remainder is uncoated.

The molds may also be constructed to impart regular or irregular, continuous or discontinuous, coatings, i.e., of various portions and patterns, to the dosage forms. For example, dimple patterned coatings, similar to the surface of a golf ball, can be formed using a molding module comprising mold insert having dimple patterns on their surfaces. Alternatively, a circumferential portion of a dosage form can be coated with one flowable material and the remaining portions of the dosage form with another flowable material. Still another example of an irregular coating is a discontinuous coating comprising holes of uncoated portions around the dosage form. For example, the mold insert may have elements covering portions of the dosage form so that such covered portions are not coated with the flowable material. Letters or other symbols can be molded onto the dosage form. Finally, the present molding module allows for precise control of coating thickness on a dosage form.

Figure 12:
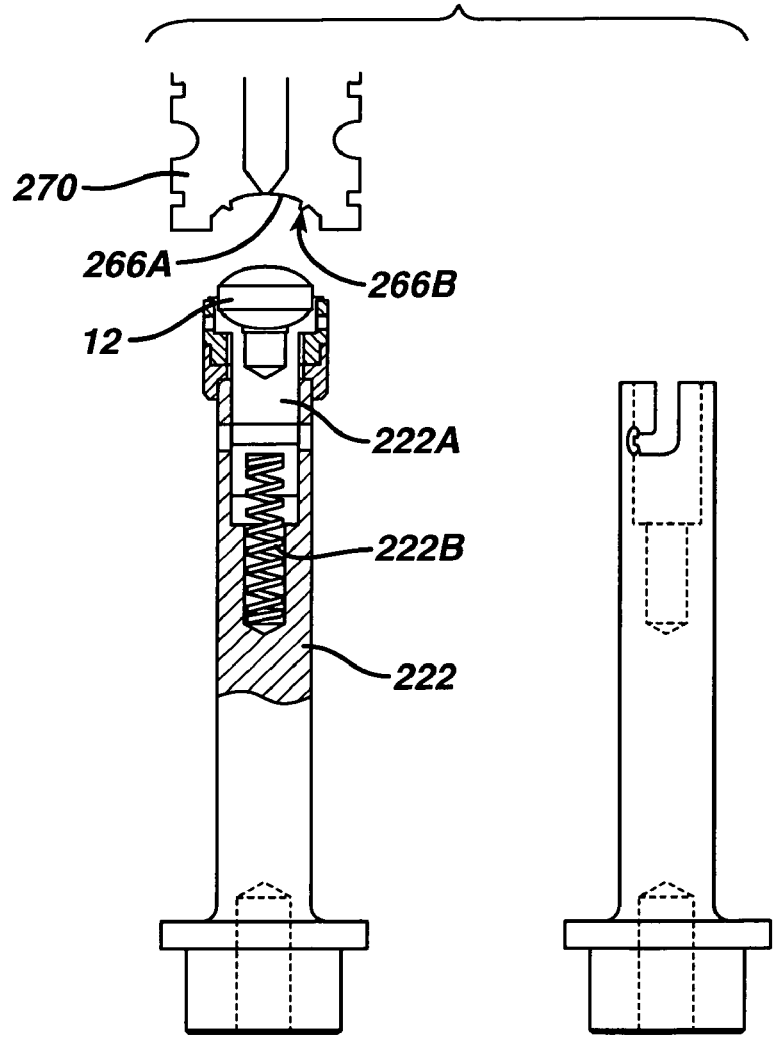
FIGS. 12 and 13 illustrate a mold shell capable of producing a discontinuous coating.
Figure 13:
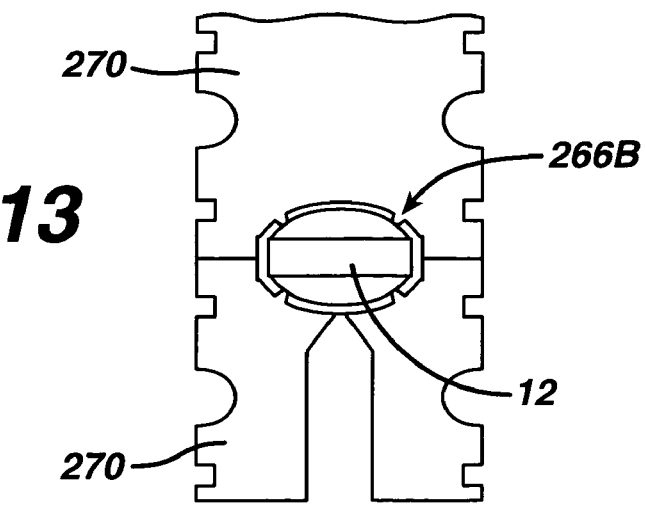

One form of a mold shell 270 having a mold cavity capable of imparting a patterned coating to the dosage form is exemplified in FIGS. 12 and 13. The mold cavity shown therein includes multiple protrusions 266B extending as fixed elements from the surface of mold shell 270 towards core 12. Such protrusions can be sized to extend part way to the core or physically touch the core. Additionally, while multiple protrusions 266B are exemplified, the effect could just as easily be achieved with only one protrusion. The shape of protrusions 266B is not significant and may form any geometric shape or representation within or through the gelatin coating.

In one embodiment, shown in FIG. 12, center support stem 222, contains a spring mechanism 222$b$ that is formed from a metal, elastomeric material, gas bladder, bevel washers, or the like; in communication with a plunger 222A. When the mold closes, at least a portion of protrusions 266B contacts compressed core 12, pressing compressed core 12 against plunger 222A, causing spring mechanism 222$b$ to compress. In one embodiment, the spring applies a pressure to seal core 12 against protrusions 266B such that when flowable material is injected in the gaps between the core and the protrusions, the areas of contact are thereby masked. The pressure applied by the spring resists an opposing pressure caused by the injection of flowable material that would otherwise tend to separate the core from protrusions or masking members 266B thereof. The compliance (or resilience or flexibility) of the spring achieves a relatively uniform masking pressure regardless of variation in core thickness.

In another embodiment, a debossed core 12, pressed by spring 222$b$ and plunger 222A against a substantially smooth mold surface 266A, will provide gaps, which will be filled with flowable material. In another embodiment, the spring may be designed (wire diameter, material, and geometry) to provide a lower force than the resultant opposing force of the pressure caused by the influx of flowable material during the injection event in order to create a partial or incomplete masking effect, such as a dimpled surface texture.

In another embodiment, flowable materials having elastic properties such as those selected from the group consisting of gels, rubbers, silicones, and the like) can provide the resilient feature to avoid breakage of the core and provide masking of the desired patterned area, eliminating the necessity for a spring. This particular embodiment is particularly useful in a 2-step molding process in which the first shell portion comprises the elastic or gel-like material, and the second shell portion includes the desired openings or surface pattern. In another embodiment, the core composition may provide sufficient ductility to avoid breakage under the pressure of the masking members (266B) of the mold surface 266A. Protrusions 266B may be pins, slots, pads, text, or the like.

In an alternate embodiment, molding of the shell may be accomplished in a single injection, eliminating the need for lower retainer 210, half of center mold 212. Cores are deposited directly into the center mold 212 and they rest upon protrusions 266B. When upper mold 214 with its mold surface 266A and protrusions 266B closes, core 12 will be suspended by such protrusions or any features on the core or mold surface, which create a flow path for the flowable material.

Closing the feed valve prematurely while injecting the first shell portion can create a unique aesthetic. This causes the first shell material to cover a portion of the first face of the core. Consequently, when the second shell flowable material is injected, it flows until it is stopped by the edge of the first shell material. The resulting dosage form has the first shell material covering a portion of a first face, and the second shell material covering the second face and the entire belly band, and a portion of the first face.

Another unique aesthetic or functionality can be created by placing a gasketing or masking device between the center mold 212 and the upper mold 214 after injection of the first shell portion and prior to closing of the upper mold against the center mold. The midsection, e.g. bellyband if the core is a compressed tablet oriented with major faces proximal to each mold surface, or a section at about the center of the longitudinal axis, if the core is a capsule-shaped form oriented with ends proximal to the center of the upper and lower mold cavities, of the resulting dosage forms may be uncoated, exposing the core surface. The exposed core surface may have the form of a continuous band, or a pattern, e.g. dots, dashes, variable thickness lines, or shapes.

Figure 11:
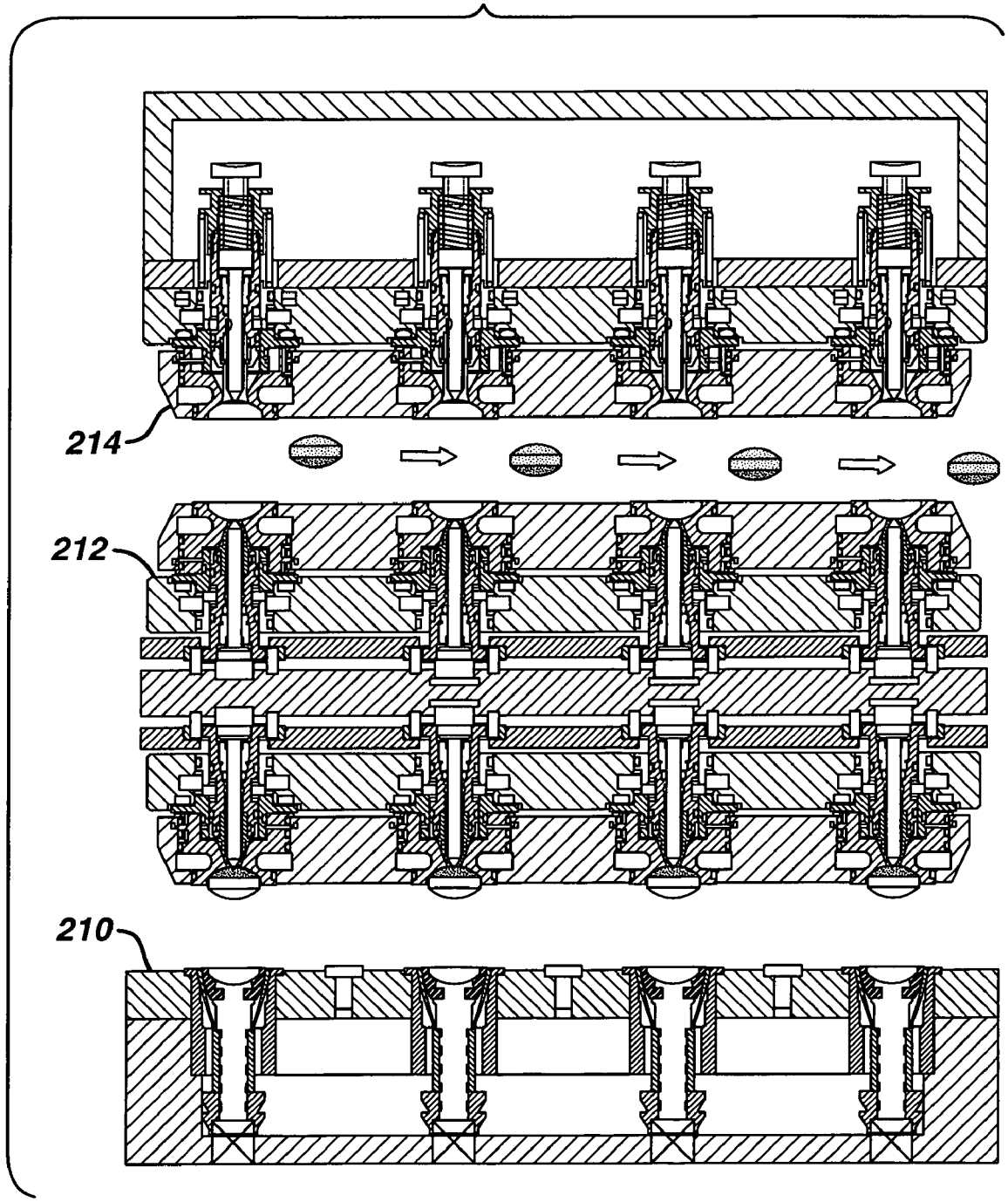

Because the flowable material is injected from above the core 12, as viewed in FIG. 11, the edge of an elastomeric collet stops flow of the flowable material. Consequently, only the portion of core 12 that is above the elastomeric collet will be coated when the lower retainer 210 and center mold assembly 210 are mated. This permits a first flowable material to be used to coat one part of the dosage form, and a second flowable material to coat the remainder of the dosage form-that portion which is beneath the elastomeric collet. Although the elastomeric collet is shaped so that about half of the dosage form will be coated at one time, the elastomeric collet can be of any desired shape to achieve a coating on only a certain portion of the dosage form.

When two halves of a dosage form are coated with different flowable materials, the two flowable materials may be made to overlap, or if desired, not to overlap. With the present invention, very precise control of the interface between the two flowable materials on the dosage form is possible. Accordingly, the two flowable materials may be made flush with each other with substantially no overlap. Or the two flowable materials may be made with a variety of edges, for example to allow the edges of the flowable materials to interlock.

The center mold assembly comprises a series of back-to-back, identical insert assemblies 230. The center mold assembly 212 rotates partially coated dosage forms from their downwardly oriented positions to upwardly oriented positions. The upwardly pointing portions of the dosage forms, which have been coated with flowable material, can now receive the remainder of their coatings once the center mold assembly 212 mates with the upper mold assembly 214. Also, the insert assemblies previously pointing upward now point downward. Thus they are now in a position to mate with the lower retainer 210 to receive uncoated dosage forms. Rotation of the center mold assembly may be accomplished, for example, using the system shown in FIG. 40 of application Ser. No. 09/966939, filed Sep. 28, 2001, now U.S. Pat. No. 6,837,696, which is incorporated herein by reference.

Each insert assembly 230 preferably comprises a stationary part, which includes a center insert 254, and a moveable part, which is in essence a nozzle and comprises a valve body 260, a valve stem 280 and valve body tip 282, as shown best in FIG. 14. Although FIGS. 14, 15 and 16 illustrate one nozzle or valve assembly, in a preferred embodiment there are preferably sixteen such nozzles or valve assemblies per center mold assembly 212, eight facing the upper mold assembly and eight facing the lower retainer. FIG. 15 depicts the insert assembly 230 in its closed position. FIG. 14 shows the insert assembly 230 positioned for injection of flowable material. FIG. 16 illustrates the insert assembly 230 in the dosage form transfer position.

The center insert 254 may be mounted to its manifold plate by any suitable means, and is preferably sealed with o-rings 262 and grooves 264 to prevent leakage of flowable material, as shown in FIG. 14. The coolant channels 238 are defined between the first manifold plate 234 and the center insert 254. The center insert 254 is constructed from a material that has a relatively high thermal conductivity, such as stainless steel, aluminum, beryllium-copper, copper, brass, or gold.

The movable portion of the insert assembly 230 includes the valve body 260, the valve stem 280, and the valve body tip 282. See FIG. 14. Valve stem 280 is independently moveable. Valve stem 280 and valve body 260 are slidably mounted within insert assembly 230. In the preferred embodiment shown, a plurality of o-rings 284 and grooves 286 seal the moveable portions of insert assembly to the stationary portion of the insert assembly. Disposed around valve stem 280 and valve body tip 282 is a flowable material path through which flowable material traveling through the second manifold plate 236 flows when the insert assembly is in the open position (FIG. 14).

Although the center mold assembly 212 is constructed with identical insert assemblies 230 on both sides of its rotary axis, each insert assembly 230 performs a different function depending on whether it is oriented in the up or in the down position. When facing down, the insert assemblies 230 are actuated to inject flowable material to coat a first portion of a dosage form. The insert assemblies 230 that are facing up are presenting partially coated dosage forms to the upper mold assembly 214. During this time, the upward facing insert assemblies are in a neutral position. Prior to the molds opening however, the upward facing insert assemblies are actuated to allow compressed air to enter the center cavity 266. This ejects the now completely coated dosage forms from the upward facing insert assemblies. Thus the completed dosage forms remain seated or held in the upper mold assembly 230.

Downward facing valve stem 280 is spring loaded to the closed position of FIG. 15 by spring 290. Downward facing valve stem 280 is moveable between the closed position of FIG. 15 and the open position of FIG. 14. Spring 290 is mounted within the valve stem 280 to spring load the valve stem 280 to the closed position.

Actuator plate 292 moves upward and opens the downward facing insert assemblies as viewed in FIG. 14 by moving and pulling the downward facing valve stems 280 against the bias of spring 290 from the position of FIG. 15 to the position of FIG. 14. Opening of the downward facing valve stems ports flowable material to dosage forms disposed between the center mold assembly 212 and the lower retainer 210. Due to the bias of spring 290, the downward facing valve stems 280 move to the closed position of FIG. 15 to stop the flow of flowable material.

When actuator plate 292 moves up as viewed in FIG. 14, the upward facing insert assemblies 230 remain stationary and closed. The upward facing valve stems 280 are compressed against spring 290 and do not open. No flowable material is provided to the upward facing insert assemblies 230. Dosage forms in the upward facing insert assemblies are coated by the upper mold assembly 214, described below. Similarly, no air is provided to the downward facing insert assemblies because dosage forms are only released from the upward facing insert assemblies.

After the flowable material has been ported and the downward facing insert assemblies 230 return to the position of FIG. 15, cam followers and an air actuator plate initiate movement of the valve body tip 282 and valve stem 280 of the upward facing insert assemblies 230. This provides a path for air through the center mold insert. In particular, the upward facing valve body tip 282 and valve stem 280 move from the position of FIG. 15 to the position of FIG. 16 due to movement of cam followers. After the application of air, cam followers move downward with the air actuator plate, permitting the upward facing insert assemblies 230 to return to the position of FIG. 15, ready for another cycle. The air actuator plate does not move the downward facing insert assemblies 230 during this cycle. They do not receive air.

FIG. 16 depicts an upward facing insert assembly 230 in the transfer position. In this position, the upward facing valve stem 280 and valve body tip 282 are withdrawn. The upward facing valve stem 280 rests against the upward facing valve body tip 282 to stop the flow of flowable material. With the valve body tip 282 withdrawn, however, air from can flow to the mold. After the dosage forms have been transferred from the center mold assembly, the air actuator plate returns up to release the upward facing valve body 260, valve body tip 282 and valve stem 280 to the closed position of FIG. 15.

Figure 17:
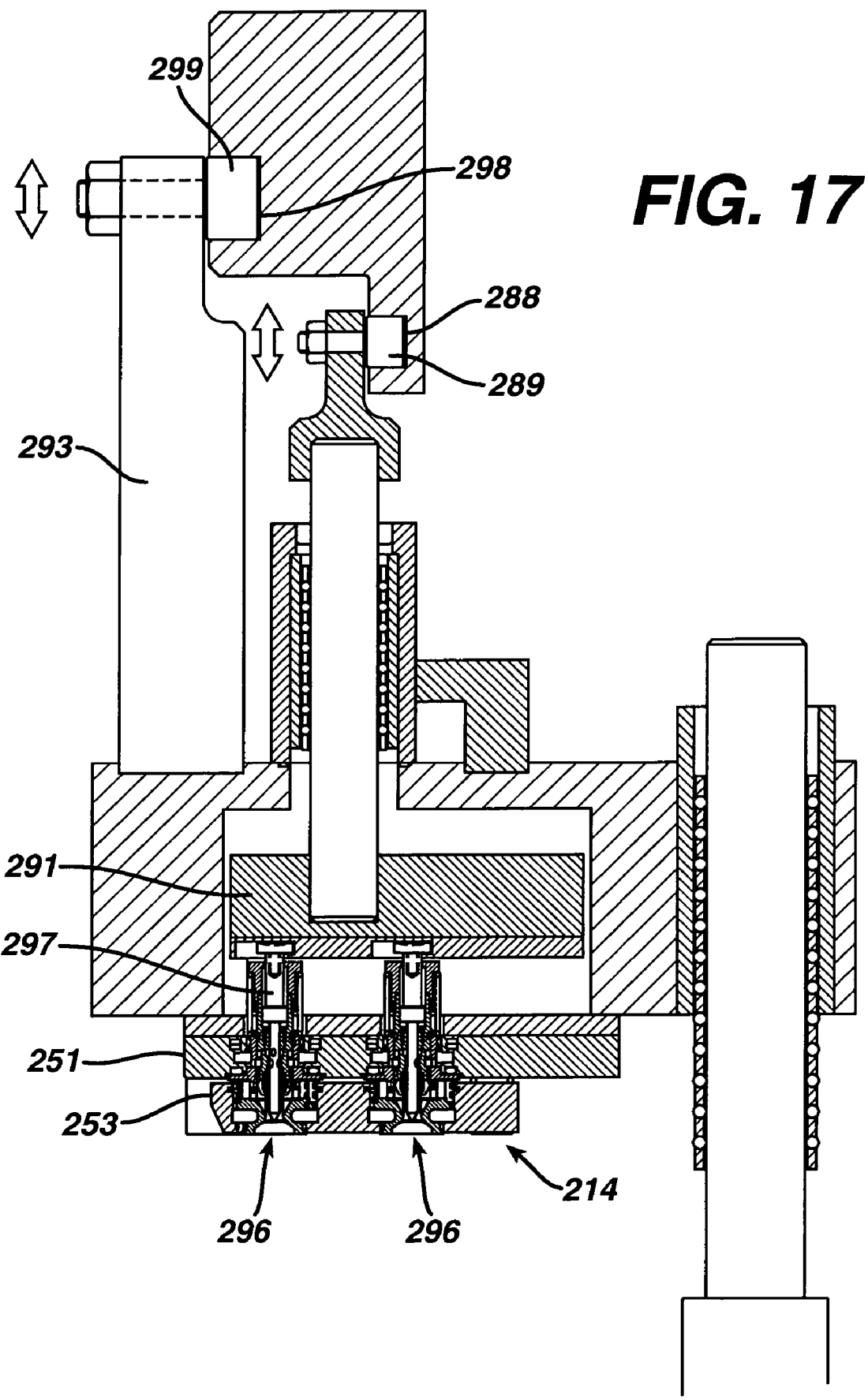
FIG. 17 is a cross-sectional view of an upper mold assembly of the injection molding module showing a cam system thereof.

The upper mold assembly 214, which is shown in FIG. 17, is similar in construction to half of the center mold assembly 212. Like the center mold assembly 212, the upper mold assembly 214 directs flowable material to at least partially coat a compressed core. In particular, the upper mold assembly 214 has a plurality of upper insert assemblies 296 (eight in the preferred embodiment) that mate with corresponding insert assemblies 230.

Although the upper mold assembly is similar to the center mold assembly, the upper mold assembly does not rotate. Rather, the upper mold assembly 214 moves vertically up and down to mate with the center mold assembly via suitable controls. Preferably, cam follower 299, cam track 298, and connector arm 293 (FIG. 17) are used to control the movement of the upper mold assembly 214. Small cam follower 289 and small cam track 288 control upper actuator plate 291. Cam follower 299, cam track 298, small cam follower 289, and small cam track 288 are similar in construction to the corresponding elements of the lower retainer 210.

The upper mold assembly 214 moves during rotation of the rotor 202 via cam follower 299 to mate with the center mold assembly 212. After this, the cam follower 299 separates the upper mold assembly 214 from the center mold assembly 212 so that the finished, fully coated dosage form can be ejected and transferred from the injection molding module as shown in FIG. 11.

The upper mold assembly 214 comprises an upper second manifold plate 251 that ports flowable material to upper insert assemblies 296 and is similar in construction to the second manifold plate of the center mold assembly 212. An upper first manifold plate 253 provides cooling to the upper insert assemblies 296 and is similar in construction to the first manifold plate of the center mold assembly 212.

A seal around each dosage form is preferably created by contact between the upward facing insert assembly 230 of the center mold assembly 212 and the upper insert assembly 296 of the upper mold assembly 214. An upper insert assembly 296 is depicted in FIGS. 18–20 in the closed, open and eject positions, respectively. Similar to the insert assemblies 230, each upper insert assembly 296 includes a stationary portion that includes an upper insert 265 and an upper flanged insert 258 and a moveable portion that is basically a nozzle. The latter comprises an upper valve body 273, upper valve stem 297 and upper valve body tip 295. The upper valve stem 297 is moveable between open and closed positions to control flow of the flowable material to the dosage form. The upper valve body, upper valve stem and upper valve body tip define the flow path for the flowable material.

One difference between the upper insert assembly 296 and the insert assembly 230 is that the upper valve body tip 295 forms part of the seal around the dosage form as shown in FIGS. 18–20 and moves outward rather than inward to eject a dosage form after it has been fully coated. FIG. 20 depicts the upper valve body tip 295 positioned to eject a dosage form. FIG. 18 depicts the upper valve body tip 295 positioned to receive a dosage form.

As the rotor 202 rotates, cam follower 289 riding in a cam track, moves up, causing the upper actuator plate 291 to rise and pull upper valve stem 297 against the bias of spring 269 and hence move it from the closed position of FIG. 18 to the open position of FIG. 19. After this, cam follower 289 moves down and causes upper actuator plate 291 to move upper valve stem 297 to the closed position of FIG. 18.

Next, cam follower 289 moves down and causes upper actuator plate 291 to move further down. When upper actuator plate 291 moves down, it depresses upper valve stem 297, which pushes upper valve body 273 and upper valve body tip 295 against the bias of spring 271. Upper valve body tip 295 thus assumes the position of FIG. 20 to eject a dosage form. In addition, as upper valve body tip 295 moves down air is ported around it from the compressed air path 267. As with the center mold assembly, compressed air in the upper mold assembly ensures that the coated dosage form does not stick to the upper insert 265 when it is ejected.

After the coated dosage form is ejected, it may be sent to a transfer device, dryer, or other mechanism. Following this, cam follower 289 and upper actuator plate 291 move back up. This in turn moves upper valve stem 297 and upper valve body tip 295 back to the position of FIG. 18 due to the bias of spring 271.

The mold assemblies, particularly mold plates 258, are maintained at a temperature below the melting or gel temperature of the flowable material. A heat sink and temperature control system are provided to regulate the temperature of the mold assemblies. Examples of heat sinks include but are not limited to chilled air, Ranque Effect cooling, and Peltier effect devices. Electrically powered Freon chillers provide the heat sink for the heat transfer fluid.

Figure 21:
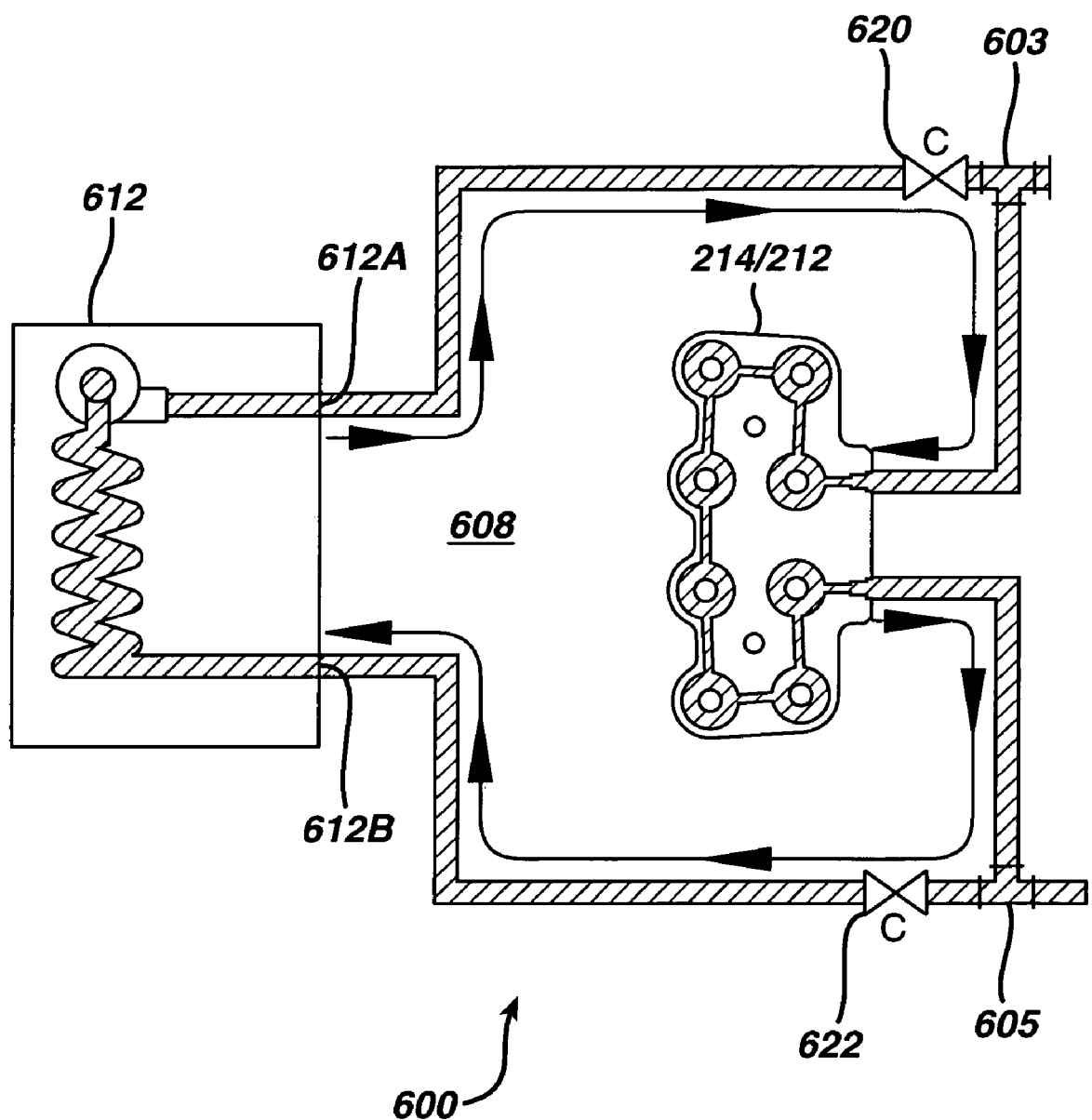
FIG. 21 illustrates a temperature control system.
Figure 22:
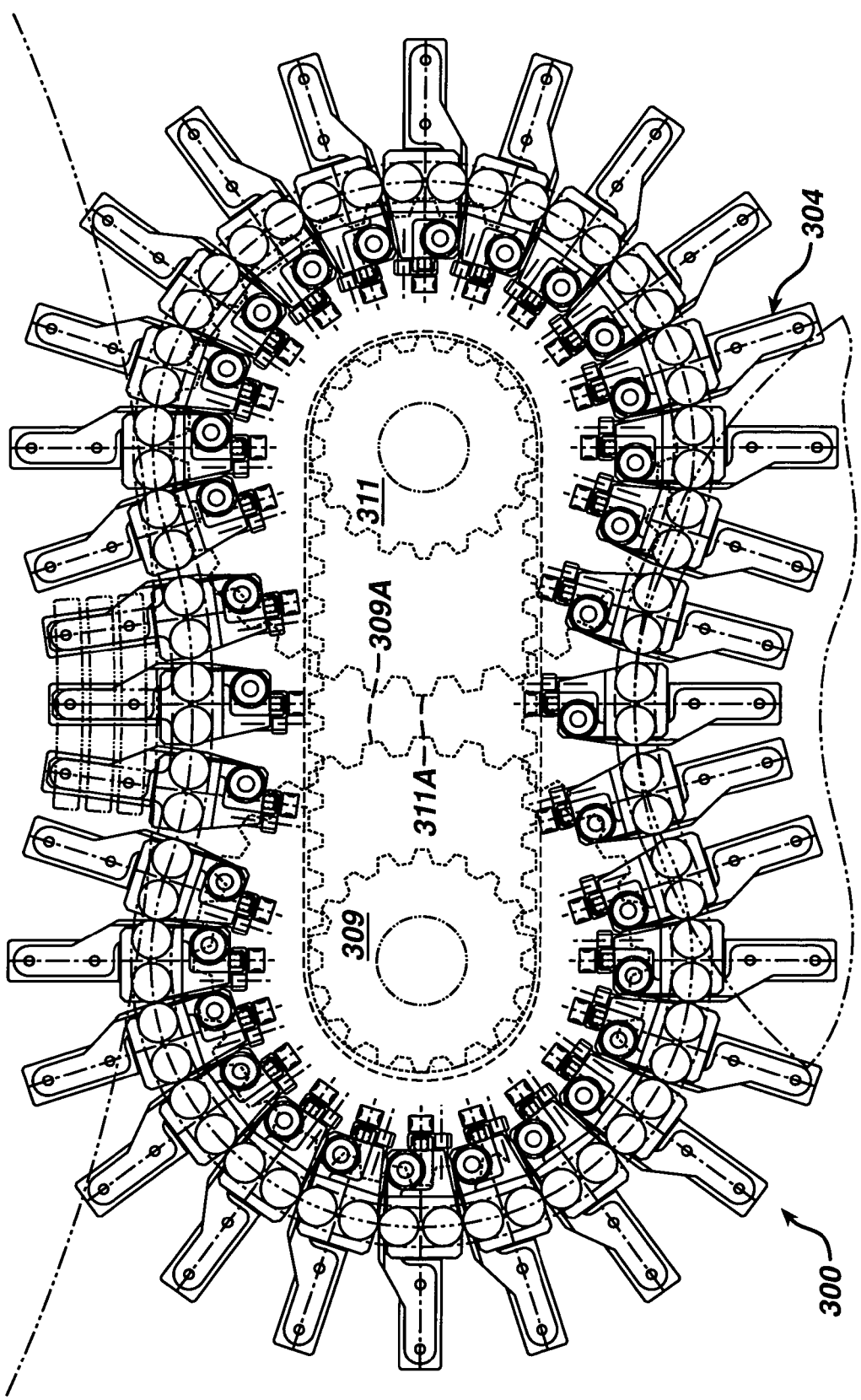
FIG. 22 is a top view of a transfer device according to the invention.

FIG. 21 depicts a temperature control system 600 for the center mold assemblies and upper mold assemblies. Although only one mold assembly 214/212 is depicted, all mold assemblies are connected to the temperature control system in a similar fashion. The tubing system includes a cold loop 608 for cooling mold assembly 214/212. Defined within the flow passageway between fitting 603 and fitting 605 is a flow path in the mold assembly 214/212. An alternative flow pattern that has been found to produce enhanced temperature control employs a single inlet passageway that splits into two distinct pathways, each pathway flowing separately in the vicinity of four mold cavities and exiting separately from the mold assembly. Valves 620 and 622, which may be solenoid or mechanically operated, control the flow of cool heat transfer fluid through the mold assembly 214/212. The system also includes a chiller 612, which provides a chilled fluid source for the cold loop. Outlet ports 612A and inlet ports 612B of the chiller can be connected to multiple molds, so that a single chiller can support all of the upper molds 214 and center molds 212.

Valves 620 and 622, when the molds are in operation, start the flow of chilled heat transfer fluid therethrough. As described above, valves 620 and 622 of the temperature control system can be of various designs known in art, such as spool, plug, ball, or pinch valves. These valves can be actuated by suitable means such as air, electrical solenoids, or by mechanical means such as cam tracks and cam followers. In one embodiment, the valves are pinch valves and are actuated by mechanical cam tracks and cam followers as the injection molding module rotates. Known pinch valves are relatively simple devices comprising a flexible section of tubing and a mechanism that produces a pinching or squeezing action on the tubing. This tubing is compressed or "pinched" to block fluid flow therethrough. Release of the tubing allows fluid to flow. Accordingly, the pinch valve functions as a two-way valve.

Known tablet presses use a simple stationary "take-off" bar to remove and eject tablets from the machine. Since the turrets of these machines rotate at fairly high speeds (up to 120 rpm), the impact forces on the tablets as they hit the stationary take-off bar are very significant. Dosage forms produced on these machines must therefore be formulated to possess very high mechanical strength and have very low friability just to survive the manufacturing process.

In contrast with prior art devices, the present transfer device is capable of handling dosage forms having a higher degree of friability, preferably containing little or no conventional binders. Thus, a preferred formulation for use with present invention comprises one or more medicants, disintegrants, and fillers, but is substantially free of binders. Dosage forms having a very high degree of softness and fragility may be transferred from any one of the operating modules of the invention as a finished product using the transfer device, or transferred from one operating module to another for further processing.

The present transfer device is a rotating device. It comprises a plurality of transfer units 304. It is preferably used for transferring dosage forms or inserts within a continuous process of the invention comprising one or more operating modules, i.e., from one operating module to another. For example, dosage forms may be transferred from a compression module 100 to an injection molding module 200, or from a thermal setting molding module 400 to a compression module 100. Alternatively, the transfer device can be used to transfer dosage forms or other medicinal or non-medicinal products between the devices used to make such products, or to discharge fragile products from such machines.

Transfer devices 300 and 700 are substantially identical in construction. For convenience, transfer device 300 will be described in detail below. Each of the transfer units 304 are coupled to a flexible conveying means, such as a belt, which may be made of any suitable material. One example of a suitable material is a composite consisting of a polyurethane toothed belt with reinforcing cords of polyester or polyparaphenylene terephthalamide (Kevlar®, E.I. duPont de Nemours and Company, Wilmington, Del.). The belt runs around the inner periphery of the device 300. The transfer units 304 are attached to the belt as described below.

The transfer device can take any of a variety of suitable shapes. However, when used to transfer dosage forms or inserts between operating modules of the present invention, transfer device is preferably generally dog bone shaped so that it can accurately conform to the pitch radii of two circular modules, enabling a precision transfer.

The transfer device can be driven to rotate by any suitable power source such as an electric motor. In a preferred embodiment, the transfer device is linked to operating modules of the invention and is driven by mechanical means through a gearbox, which is connected, to the main drive motor 50. In this configuration the velocity and positions of the individual transfer units of the transfer device can be synchronized with the operating modules. In a preferred embodiment the drive train includes a drive pulley 309 and an idler pulley 311 which are in the preferred embodiment disposed inside of the transfer device 300. The drive shaft 307 connects the main drive train of the overall linked system to the drive pulley 309 of the transfer device. The drive shaft 307 drives the drive pulley 309 to rotate as shown in FIG. 3. The drive pulley 309 has teeth 309A that engage teeth disposed on the interior of belt, which in turn rotates the transfer device. The idler pulley 311 has teeth 311A that engage belt, which causes the idler to rotate with the belt. Other flexible drive systems, such as chains, linked belts, metal belts, and the like can be used to convey the transfer units 304 of the transfer device 300.

The radii of the cam track, the pitch distance between the transfer units, the pitch of the toothed belt, and the gear ratio between the drive pulley and the main drive of the linked system are all selected such that the transfer device is precisely aligned with the operating modules linked to it. As each operating module rotates, the transfer device remains synchronized and phased with each, such that a precise and controlled transfer from one operating module to another is achieved. The velocity and position of the transfer unit is matched to the velocity and position of the operating module along the concave portions of the cam track. Transfers are accomplished along this arc length. The longer the length of the arc, the greater the time available to complete a transfer.

Dosage forms that have been coated with flowable material in the injection molding module are relatively hard compared with dosage forms that have coated using conventional dipping processes. Thus, the amount of drying needed after molding a coating onto a dosage form using the injection molding module is substantially less than that required with known dipping processes. Nevertheless, they may still require hardening, depending upon the nature of the flowable material.

Preferably, dosage forms coated in the injection molding module are relatively hard so that they can be tumble hardened relatively quickly. Alternatively, an air dryer may be used. Any suitable dryers may be used, while a variety of such dryers are generally understood in the art.

What is claimed is:

1. A method of making a coated dosage form comprising:
  a) introducing a core into a mold shell;
  b) injecting a flowable material under pressure into the mold shell;
wherein the mold shell has an interior surface capable of providing a discontinuous coating around said dosage form.

2. The method according to claim 1, wherein said mold shell has an interior surface with at least one protrusion that extends toward the core.

3. The method according to claim 1, wherein said mold shell has an interior surface with a plurality of protrusions that extend toward and touch the surface of the core.

4. The method according to claim 3, wherein the plurality of protrusions are an integral and inseparable part of the mold shell.

5. The method according to claim 3, wherein the core is a compressed powder containing a medicant.

6. A method of making a coated dosage form, comprising the steps of:
  a) compressing a powder material into a compressed core in a compression module;
  b) transferring said compressed core from the compression module to an injection molding module;

c) injecting a flowable material into a mold shell having an interior surface capable of providing a discontinuous coating around said compressed core; and d) hardening said flowable material so as to form a discontinuous coating over said compressed core;

wherein steps (a) through (d) are linked together such that essentially no interruption occurs between said steps.

7. The method of claim 6, wherein one or more of said steps is performed on a continuous basis.

8. The method according to claim 6, wherein said mold shell has an interior surface with at least one protrusion that extends toward the compressed core.

9. The method according to claim 6, wherein said mold shell has an interior surface with a plurality of protrusions that extend toward and touch the surface of the compressed core.

10. The method according to claim 9, wherein the plurality of protrusions are an integral and inseparable part of the mold shell.

11. The method of claim 9, wherein said powder material contains a medicant.

12. The method of claim 6, wherein steps (a) through (d) are performed simultaneously, such that while coatings are being hardened on a first group of compressed cores in step (d), flowable material is being molded around a second group of compressed cores in step (c), a third group of compressed cores are being transferred to said injection molding module in step (b), and a fourth group of compressed cores are being formed in step (a).

13. The method according to claim 11, wherein said flowable material comprises a gelatin.

14. The method according to claim 6, wherein step (c) comprises the steps of:

(i) injecting into a first mold shell a first flowable material around a first portion of said compressed core; and (ii) injecting into a second mold shell a second flowable material around a second portion of said compressed core, wherein either the first mold shell or the second mold shell or both mold shells have a surface capable of producing a discontinuous coating over at least a portion of said compressed core.

15. A linked apparatus for making dosage forms containing a medicant, comprising:

a) a compression module having means for forming compressed cores by compressing a powder containing said medicant;

b) a transfer device having means for continuously transferring said compressed cores from said compression module to an injection molding module; and c) an injection molding module having means for continuously molding a coating of flowable material over said compressed cores that comprises a mold shell having a surface capable of producing a discontinuous coating over said compressed cores.

16. The apparatus according to claim 15, further comprising means for operating said compression module, said transfer device, and said injection molding module simultaneously, such that as coatings are being molded on a first group of compressed cores in said injection molding module, said transfer device transfers a second group of compressed cores to said injection molding module, and said compression module forms a third group of compressed cores.

17. The apparatus according to claim 15, wherein said means for continuously molding a coating over said compressed cores comprises:

(i) first molding means for molding a first flowable material around first portions of said compressed cores comprising a first mold shell; and (ii) second molding means for molding a second flowable material around second portions of said compressed cores comprising a second mold shell;

wherein either said first mold shell or second mold shell or both mold shells have an interior surface capable of producing a non-uniform coating over said compressed core.

18. The apparatus according to claim 15, wherein (i) said compression module comprises a die table mounted for rotation about a first axis and having a plurality of die cavities disposed around the perimeter thereof, whereby rotation of said die table carries said die cavities around a first circular path, and (ii) wherein said injection molding module comprises a rotor mounted for rotation about a second axis and comprising a plurality of mold cavities disposed around the perimeter thereof, whereby rotation of said rotor carries said mold cavities around a second circular path.

19. The apparatus according to claim 18, wherein said transfer device comprises a flexible conveying means traversing around a third path, a first portion of said third path being coincident with said first circular path, and a second portion of said third path being coincident with said second circular path.

* * * * *